(12) United States Patent
Uri et al.

(10) Patent No.: US 9,176,064 B2
(45) Date of Patent: Nov. 3, 2015

(54) BISUBSTRATE FLUORESCENT PROBES FOR PROTEIN KINASE CK2

(71) Applicant: University of Tartu, Tartu (EE)

(72) Inventors: Asko Uri, Tartu (EE); Kaido Viht, Tartu (EE); Erki Enkvist, Tartu (EE); Ekambaram Ramesh, Tartu (EE)

(73) Assignee: UNIVERSITY OF TARTU, Tartu (EE)

( * ) Notice: Subject to any disclaimer, the term of this patent is extended or adjusted under 35 U.S.C. 154(b) by 0 days.

(21) Appl. No.: 13/975,934

(22) Filed: Aug. 26, 2013

(65) Prior Publication Data
US 2014/0057291 A1 Feb. 27, 2014

(30) Foreign Application Priority Data

Aug. 24, 2012 (EP) ..................... 12181818

(51) Int. Cl.
| | |
|---|---|
| *C07D 487/04* | (2006.01) |
| *C07D 517/04* | (2006.01) |
| *C07D 403/12* | (2006.01) |
| *C07D 405/12* | (2006.01) |
| *G01N 21/64* | (2006.01) |
| *C07D 403/14* | (2006.01) |
| *C07D 493/10* | (2006.01) |
| *C09B 11/24* | (2006.01) |
| *C09B 23/08* | (2006.01) |
| *C07K 7/06* | (2006.01) |
| *C12Q 1/48* | (2006.01) |
| *C12N 9/12* | (2006.01) |

(52) U.S. Cl.
CPC .......... *G01N 21/6486* (2013.01); *C07D 403/14* (2013.01); *C07D 493/10* (2013.01); *C07K 7/06* (2013.01); *C09B 11/24* (2013.01); *C09B 23/08* (2013.01); *C12N 9/12* (2013.01); *C12Q 1/485* (2013.01)

(58) Field of Classification Search
None
See application file for complete search history.

(56) References Cited

PUBLICATIONS

Enkvist et al., "A subnanomolar fluorescent probe for protein kinase CK2 interaction studies", Organic & Biomolecular Chemistry, 2012, 10, pp. 8645-8653.

*Primary Examiner* — Michael Barker
(74) *Attorney, Agent, or Firm* — Birch, Stewart, Kolasch & Birch, LLP

(57) ABSTRACT

This invention relates to fluorescent probes for screening and characterization of compounds binding to protein kinase CK2, measurement of concentration of the catalytically active form of CK2 and imaging of CK2 activity in cells and tissues. The CK2-selective probe of the present invention interacts with binding sites of both substrates of the catalytic subunit of CK2 and therefore can be used for characterization of all inhibitors binding to the active site of CK2 in the binding/displacement assay. The high affinity of the probe affords the detection of the enzyme at low concentration and characterization of inhibitors in a wide affinity range. The invention also relates to the application of the probes for mapping and monitoring of CK2 activity in cells, tissues and live organisms.

16 Claims, 4 Drawing Sheets

BISUBSTRATE FLUORESCENT PROBES FOR PROTEIN KINASE CK2

FIELD OF THE INVENTION

The invention concerns novel fluorescent probes binding with high affinity to the active site of the protein kinase CK2 and the application of the probes for screening of compounds and evaluation of inhibitors targeted both to the nucleotide-binding pocket or/and protein/peptide substrate-binding domain of the kinase, and methods of manufacturing of such probes. The invention also relates to the application of the probes in screening assay for identifying compounds that bind to and modulate the activity of protein kinase CK2. The invention relates to the assay for determination of the concentration of protein kinase CK2, identification and characterization of compounds binding to the active site of this kinase. The invention also relates to the application of the probes for mapping and monitoring of CK2 activity in cells, tissues and live organisms.

BACKGROUND TO THE INVENTION

Protein kinases (PKs) are enzymes that play a key role in the regulation of protein functions in living cells. There are 538 protein kinase-encoding genes in human genome [Schwartz et al., Bioorg. Chem. 39 (2011) 192] and it has been estimated that the activity of one third of proteins is regulated by phosphorylation. More than 400 human diseases (including several forms of cancer) have been linked to aberrant protein kinase signaling. This has made PK an important drug target [Cohen, Nat. 20 Rev. Drug Discov. 1 (2002) 309; Fischer, Curr. Med. Chem. 11 (2004) 1563; Schwartz et al., Bioorg. Chem. 39 (2011) 192].

Three kinds of active site-targeted inhibitors of protein kinases are known. The first type of inhibitor is targeted to the nucleotide binding site of PK. Since the nucleotide binding pocket of protein kinases is highly conserved, the development of selective inhibitors of this type is problematic. In addition, these inhibitors have to compete with a high concentration of ATP in the cellular milieu. The second type of active site targeted inhibitors of PKs comprise compounds that associate with the peptide/protein binding site of PK [Bogoyevitch et al., Biochim. Biophys. Acta. 1754 (2005) 79; Lawrence, Handb. Exp. Pharmacol. 167 (2005) 11-44]. The third type is bisubstrate inhibitors that simultaneously associate with the nucleotide and peptide/protein binding sites [recent review: Uri et al., Biochim. et Biophys. Acta 1804 (2010) 541]. Bisubstrate (or biligand) inhibitors have been constructed by combining two fragments, nucleotide analogue or small molecule nucleotide-competitive inhibitor targeted to the nucleotide-binding pocket of PK, and peptide or peptide mimetic, targeted to the peptide/protein binding site of PK. These two fragments are covalently conjugated via a linker, which allows effective association of both of these fragments with the active site of PK. Bisubstrate inhibitor approach could lead to enhanced specificity and potency of inhibition. The most potent bisubstrate inhibitors described are ARC-type inhibitors developed by the authors of the present invention, which show subnanomolar to picomolar potency towards basophilic protein kinases [U.S. Pat. No. 8,158,376; EE200300187; Enkvist et al., J. Med, Chem. 49 (2006) 7150; Viht et al., Anal. Biochem., 362 (2007) 268; Enkvist et al., Bioorg. & Med. Chem. Lett. 19 (2009) 6098; Lavogina et al. J. Med. Chem. 52 (2009) 52, 308; Lavogina et al. Biochim. et Biophys. Acta 1804 (2010) 1857; Enkvist et al. ACS Chem Biol. 10 (2011) 1052]. These inhibitors are constructed by conjugating ATP binding site targeted adenosine-5'-carboxylic acid (Adc) or ATP-competitive inhibitor and the protein substrate domain directed oligo-(L-arginine) or oligo-(D-arginine) via a hydrophobic linker.

Protein kinase CK2 is an acidophilic serine/threonine kinase, which regulates a number of cellular processes. The activity of CK2 is involved in cell growth, proliferation, angiogenesis and suppression of apoptosis, making the kinase a potential target for cancer chemotherapy [Trembley et al., Cell. Mol. Life Sci. 66 (2009) 1858]. In cells, CK2 is mostly present in the form of the holoenzyme, a heterotetramer composed of two catalytic (α and/or α') and two regulatory (β) subunits [Salvi et al., FEBS Lett., 580 (2006) 3948; Niefind et al., EMBO J. 20 (2001) 5320].

Several selective ATP-competitive inhibitors of CK2 have been developed [Cozza et al., Curr. Med. Chem. 20 (2013) 671]. A highly potent and orally available nucleotide-competitive inhibitor CX-4945 is in clinical trials for cancer treatment [Pierre et al., J. Med. Chem. 54 (2011) 635]. Non-ATP-competitive inhibitors of CK2 [Laudet et al., Biochem. J. 408 (2007) 363; Moucadel et al., Oncotarget, 2 (2011) 997] and biligand inhibitors with modest micromolar inhibitory potency [Swider et al., Moll. Cell. Biochem. 356 (2011) 117] have also been described but the inhibitory potency of the disclosed compounds is too low for practical applications.

The evaluation of the structure and functioning of protein kinases and development of potent inhibitors as drug candidates and biomedical research tools requires sensitive detection methods. The majority of kinase inhibitors are evaluated by their inhibitory potencies ($IC_{50}$) in kinetic studies. The radiometric assay that is based on transfer of radioactively labeled phosphoryl group from [$\gamma$-$^{32}$P] ATP to peptide or protein substrate has been considered the gold standard format because of high sensitivity and direct readout of the catalytic activity of kinase. However, such assay involves labour intensive separation steps and is hazardous due to radioactivity. Fluorometric methods have been developed that are better spatially and temporally focused than radiometric methods, and as such, are better suited for HTS applications. One type of such fluorometric assays is based on the capture of the product of the phosphorylation reaction by an antibody or other macromolecule (e.g., IMAP-particle) that changes the fluorescent properties of the label attached to the substrate of the phosphorylation reaction or that displaces fluorescent reporter molecule from the complex with the macromolecule, changing fluorescence properties such as intensity or anisotropy. Although better suited for HTS format, these types of assay still require effective substrate for the phosphorylation reaction and high-affinity capture particles. An alternative way to characterize the inhibitors of protein kinases is by their binding affinities to the active sites of the enzymes. The dissociation constants ($K_d$) for the inhibitor-kinase complexes are independent of the $K_m$ values of the substrates and are thus better comparable for different kinases using different assay setups. These assay formats utilize a fluorescent reporter molecule—fluorescent probe—that changes its fluorescence properties intensity, anisotropy, lifetime) upon binding to the active site of the PK. Competitive inhibitors displace the probe from the complex with protein kinase resulting in the change of fluorescence characteristics. In addition to the characterization of inhibitors of protein kinases, the fluorescent probes can be applied for detection and quantification of the active forms of PKs in enzyme preparations and biological compositions (cell lysates, cells or tissues).

Although several high-affinity fluorescent probes for protein kinases have been described [Chen et al., J, Biol, Chem. 268 (1993) 15812, WO2005/033330, US2006/0263841], no such examples for protein kinase CK2 have been reported. Generic high-affinity fluorescent probes for protein kinases have been described by the authors of the present invention [U.S. Pat. No. 8,158,376; Vaasa et al. Anal. Biochem. 385

(2009) 85-93; Enkvist et al. ACS Chem. Biol. 10 (2011) 1052], but these compounds have shown selectivity towards basophilic protein kinases and no binding to protein kinase CK2 with these probes have been observed.

SUMMARY OF THE INVENTION

This invention relates to a selective active site-targeted fluorescent probes for protein kinase CK2 for identification of compounds binding to protein kinase CK2, for measurement of the affinity of inhibitors of protein kinase CK2, and determination of the active concentration of protein kinase CK2. The probe binds simultaneously to both the nucleotide-binding site and to the peptide/protein binding site of the catalytic subunit of protein kinase CK2 and thus enables the evaluation of inhibitors targeted to either or both of these binding sites. The high affinity of the probe (KD from 0.02 to 10 nM, depending on the chosen structure) affords the application of the enzyme at very low concentration (0.5 nM) which leads to the substantial decrease of the consumption of the kinase. The probe is applicable for exact determination of binding constants for inhibitors with nanomolar and micromolar affinity in displacement experiments. The probe is very selective towards protein kinase CK2 and thus affords discrimination of interactions of inhibitors with protein kinase CK2 from their interaction with other kinases.

DETAILED DESCRIPTION OF INVENTION

Figure 1:
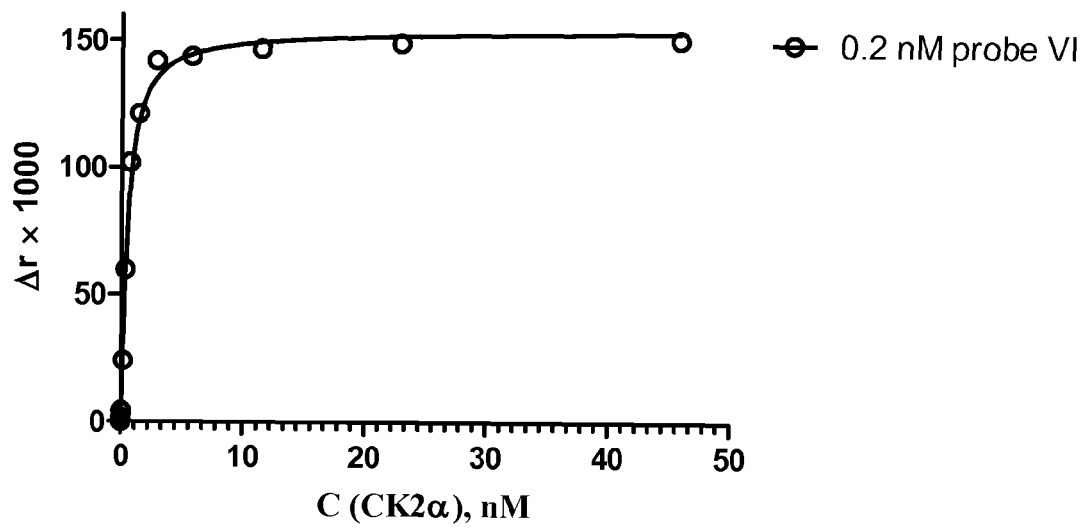
FIG. 1. Titration of the fluorescent probe VI at 0.2 nM concentration with CK2α detected by anisotropy change.

The present invention relates to bisubstrate fluorescent probes that change fluorescence properties (intensity, anisotropy, life-time) upon binding to the catalytic site of protein kinase casein kinase 2 (CK2), and application of such probes for detection and quantification of the active form of CK2 in assay buffers and in biological compositions (cell lysates, cells or tissues), identification of inhibitors of CK2 and characterization of the binding affinity of these inhibitors.

Definition: In the meaning of the present invention, the terms CK2, casein kinase 2 or protein kinase CK2 refer to serine/threonine-selective protein kinase known as casein kinase 2 (EC 2.7.11.1), which may be in the form of a free (α or α') catalytic subunit or in the form of the holoenzyme or in complex with other proteins. The assays can be performed with native isoforms CK2 as well as chemically, enzymatically and genetically modified versions of the isoforms of casein kinase CK2, including mutated, labeled, fused and truncated forms incorporating the catalytic domain.

The fluorescent probes of the present invention have very high affinity (KD=0.02 . . . 10 nM), which enables the application of low concentrations of kinase and determination of binding constants for inhibitors with high affinity [Uri et al., Biochim. Biophys. Acta 1804 (2010) 541-546]. The fluorescent probes associate simultaneously with the nucleotide and peptide/protein binding regions of the catalytic subunit of CK2 and compete with inhibitors targeted to either or both of these binding sites. Very high selectivity of the probes enables to distinguish protein kinase CK2-related interactions in complicated biological systems.

Benefits of the Presented Invention

The fluorescent probe of the present invention has very high affinity for protein kinase CK2 (KD=0.02 . . . 10 nM) for which no such high-affinity fluorescent probes have been reported so far. The high affinity of the probes makes it possible to use the fluorescent probe in binding assays for the detection and quantification of protein kinase CK2, monitoring of the localization of CK2 in live cells, imaging of CK2 activity in tissue samples and identification and characterization of inhibitors binding to the active site of CK2, and in displacement assays for the identification and characterization of inhibitors of CK2. The probe of the present invention binds both to the nucleotide binding site and peptide/protein binding site of CK2 and can be used for the characterization of inhibitors of CK2 targeted to both of these binding sites.

Fluorescent Probes

The fluorescent probe of the present invention has the general formula:

$$X\text{-}Y\text{-}Z\text{-}L\text{-}FL \qquad (I)$$

wherein X-Y-Z is a bisubstrate inhibitor binding to the catalytic site of protein kinase CK2, in which X is a multi-cyclic organic compound targeted to the nucleotide binding pocket of the kinase, Z binds to the peptide/protein-binding domain of the kinase, Y is a tether that connects X and Z and permits the simultaneous binding of X and Z to the active site of the kinase; FL is a fluorescent dye, whose optical characteristics are changed in the course of the binding of the probe to CK2; and L is a linker between the bisubstrate inhibitor and fluorescent dye.

More specifically, the fluorescent probe of the present invention has the general structure:

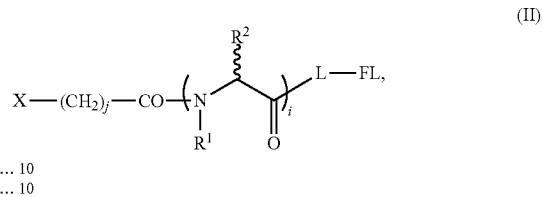

$j = 1 \ldots 10$
$i = 1 \ldots 10$

Where the fragment X is targeted to the nucleotide-binding pocket of protein kinase CK2 and it may be derived from nucleotide analogues or nucleotide-competitive inhibitors of CK2 known in the art [for examples, see Sarno et al., Biochim. Biophys. Acta. 1754 (2005)263-270 and Sarno et al., Curr. Top. Med. Chem. 11 (2011) 1340-1351], $R^1$ and $R^2$ are either H or —$(CH_2)_n$COOH independently for each oligomer unit, where n is 0 . . . 3. The number of free carboxyl groups among the substituents $R^1$ and $R^2$ in the whole structure of the probe should be at least 1. The α-carbon connected to group $R^2$ may be either in R or S configuration independently in each oligomer unit.

In one embodiment of the probe the structure of the fragment X of the formula I is derived from 4,5,6,7-tetrabromo-1H-benzimidazole (TBBI), a moderately potent and very selective ATP-competitive inhibitor of CK2 [Zień et al., Biochem. Biophys. Res. Commun. 306 (2003) 129-133] that is defined by the formula III, wherein $R^3$, $R^4$, $R^5$ and $R^6$ are bromo substituents. The fragment X may also be a derivative of 1H-benzimidazole, wherein $R^3$, $R^4$, $R^5$ and $R^6$ are independently H, Br or I in any combination.

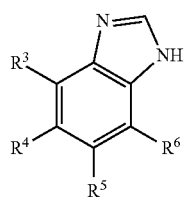

(III)

In another embodiment of the probe, the structure of the fragment X of the formula I is derived from 5-hydroxybenzo[c][2,6]naphthyridine-8-carboxylic acid, that is defined by the formula IV.

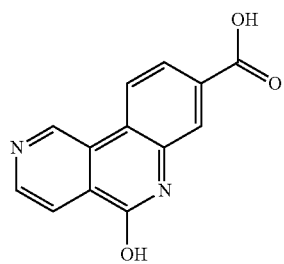

(IV)

In another embodiment, the structure of the fragment X of the formula I incorporates a sulfur, selenium or tellurium containing aromatic ring leading to responsive long lifetime luminescent probes as it has been described previously by the authors of the present invention [Enkvist et al., ACS Chem. Biol. 6 (2011) 1052-1062 and in a patent application EP2482072]. In the case of such probes their binding to the target kinase leads to long lifetime (in microsecond range) luminescence signal when phosphorescence donor of X is excited in near UV-region and emission is measured at emission wavelengths of the fluorescent dye FL. More specifically the fragment X of the formula I may be derived from 8H-[1,2,5]selenadiazolo[3,4-g]indole, that is defined by the formula V, wherein Q is Se. The fragment X may also be derived from 8H-[1,2,5]thiadiazolo[3,4-g]indole or 8H-[1,2,5]telluradiazolo[3,4-g]indole, defined by the formula V wherein Q is either S or Te, respectively.

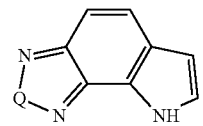

(V)

The fragment Z in the general formula I is targeted to the protein-binding region of protein kinase CK2 and it is a peptide or a peptide analogue that mimic the substrates of CK2 [Meggio et al., FASEB J. 3 (2003) 349-368]. More specifically the fragment Z is a peptide containing multiple amino acid residues selected from L-aspartic acid, D-aspartic acid, L-glutamic acid or D-glutamic acid in any combination. The fragment Z may also be a peptide analogue e.g., peptoid, containing one or more carboxylic acid groups in the side chains. The fragment Y is a tether connecting the fragments X and Z that permits simultaneous association of X and Z to the active site of the kinase in optimal orientation. Preferably the fragment Y is derived from octanoic acid, but Y may also be a group providing a chain of 1-20 atoms, including a straight or branched hydrocarbon chain of 1-20 carbon atoms, wherein one or more $CH_2$ groups are optionally and independently replaced with —O—, —S—, —N(R)—, —P(O)(R)—, —OP(O)O—, —S(O)—, SO2-, —C(O)—, —C(O)N— or —C(O)O—, where R is H or a hydrocarbon consisting of 6 carbons. The high affinity and selectivity of the probe is achieved in cooperation of the fragments X, Y and Z. The aim of the linker L is the positioning of the fluorescent label FL in the position where it causes minimal hindrance to the binding of the inhibitory fragment of the probe X-Y-Z to the kinase, but at the same time affords change of fluorescence properties of the label when the probe is bound to the enzyme. The fragment L may be a direct bond or a chain of 1-20 repeating units of hydrocarbon with straight of branched structure containing 1-20 atoms, wherein one or more carbons may be replaced with O, S, N or P atoms.

The choice of fluorescent label depends on the detection instrumentation. Fluorescent labels useful in the present invention include any of those known in the art and which change fluorescence properties (intensity, lifetime, anisotropy) upon binding of the probe to the catalytic pocket of the kinase. It is preferred that the fluorescence label has high brightness, photostability and it fluoresces at long wavelength (above 600 nm) to avoid interference from autofluorescence of biological compositions and tested inhibitors. Examples of fluorescent labels suitable for the present invention include fluorescein and fluorescein derivatives, rhodamine and rhodamine derivatives such as tetramethylrhodamine, AlexaFluor® and BODIPY® dyes, cyanine dyes such as Cy™— and PromoFluor® dyes and quantum dots. In another embodiment of the invention, the fluorescent probe of the invention is present in the form of salt, or in a caged or prodrug form that releases the probe in response to external trigger such as exposition to enzymatic activity or light flash.

The probe of the invention can be used for in vitro, in vivo and ex vivo determination of protein kinase CK2 activity.

Also, the invention is related to a method for the identification of a kinase inhibitor by displacement of the fluorescent probe of the invention from its complex with the kinase by an inhibitor compound, which comprises the steps of (i) establishing the KD for the complex of the fluorescent probe with the kinase, (ii) contacting the fluorescent probe with the kinase and measuring the fluorescence signal of the formed complex, (iii) incubating the complex formed in the previous step with the potential inhibitory compound or a mixture of compounds and (iv) measuring of the fluorescence signal of the probe, and comparing the fluorescence signals from step (ii) and step (iii), and the difference in these fluorescence signals indicates the presence of an active compound in the probe of the step (iii).

The fluorescent probe of the invention is also used in the method for the determination of binding characteristics of protein kinase inhibitors by displacement of the fluorescent probe of the invention from its complex with the kinase by an inhibitor compound comprising the steps of: (I) establishing the KD for the complex of the fluorescent probe with the kinase; (II) contacting the fluorescent probe with the kinase and measuring the fluorescence signal of the fanned complex; (III) incubating of the complex formed in the previous step with a series of different concentrations of the inhibitory compound and measuring of the fluorescence signal at each concentration of the inhibitor; (IV) calculating of the Kd of the inhibitory compound for its binding to the active site of the kinase proceeding from the KD for the complex of the fluorescent probe with the kinase and the results of the measurements of the step III. The signal in said method can be measured as a shift in fluorescence polarization of the probe. The fluorescence signal to be measured can be fluorescence intensity, fluorescence lifetime, fluorescence resonance energy transfer, fluorescence correlation, or fluorescence intensity distribution. The screening for such protein kinase CK2 inhibitors can be performed on a multi-well plate.

Yet another method for the determination of binding characteristics for compounds targeting the ATP-binding pocket of the kinase by displacement of the fluorescent probe of the invention from its complex with the kinase by an inhibitor compound comprises the steps of: (I) establishing the KD for the complex of the fluorescent probe with the kinase; (II) contacting the fluorescent probe with the kinase and measuring the fluorescence signal of the formed complex; (III) incubating of the complex formed in the previous step with a series of different concentrations of the inhibitory compound and measuring of the fluorescence signal at each concentration of the inhibitor; (IV) calculating of the Kd of the inhibitory compound for its binding to the ATP binding site of the kinase proceeding from the KD for the complex of the fluorescent probe with the kinase and the results of the measurements of the step III.

Moreover, a method for the determination of binding characteristics for compounds targeting the protein/peptide substrate binding domain of the kinase by displacement of the fluorescent probe of the invention from its complex with the kinase by an inhibitor compound comprises the steps of: (I) establishing the KD for the complex of the fluorescent probe with the kinase; (II) contacting the fluorescent probe with the kinase and measuring the fluorescence signal of the formed complex; (III) incubating of the complex formed in the previous step with a series of different concentrations of the inhibitory compound and measuring of the fluorescence signal at each concentration of the inhibitor; (IV) calculating of the Kd of the inhibitory compound for its binding to the substrate protein/peptide binding domain of the kinase proceeding from the KD for the complex of the fluorescent probe with the kinase and the results of the measurements of the step III.

Still another method for quantifying the kinase in a sample is characterized by bringing the fluorescent probe of the invention into contact with the sample and measuring of the fluorescence anisotropy from the probe: (I) establishing the KD for the complex of the fluorescent probe with the kinase; (II) contacting the fluorescent probe with a series of samples of the kinase at different dilutions and measuring the fluorescence signal of the formed complex of the diluted samples; (III) calculating the fraction of the active (binding) form of the kinase in solution.

Based on the above, a kit can be compiled to perform a method of identification of inhibitors of protein kinases or determination of binding characteristics of inhibitors, comprising a fluorescent probe of the present invention.

Examples of the structures of fluorescent probes of the present invention include but are not limited to:

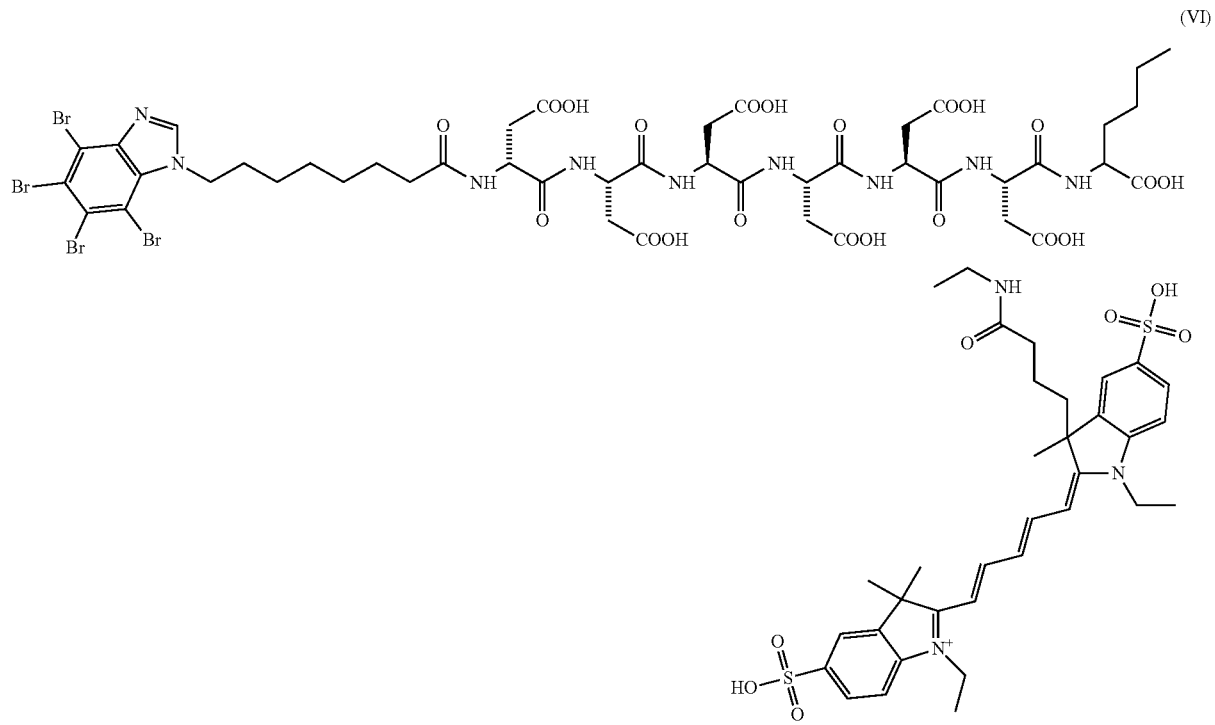

(VI)

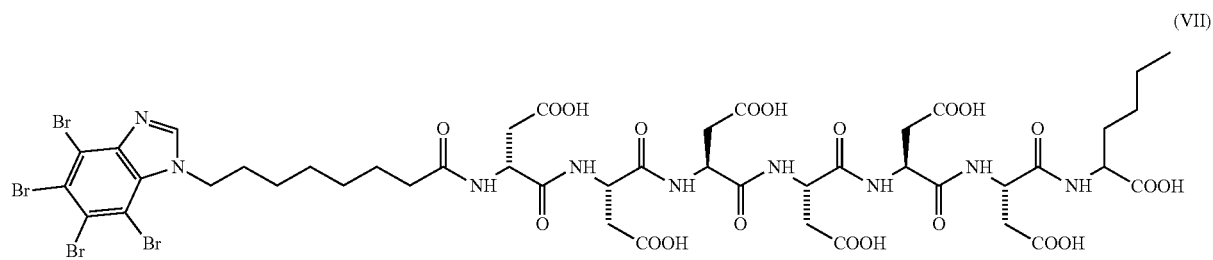
(VII)
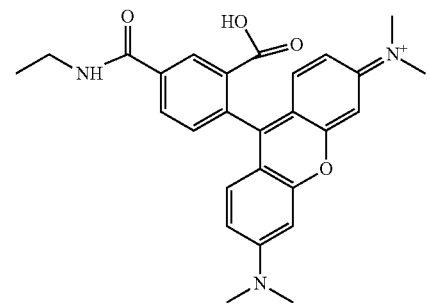
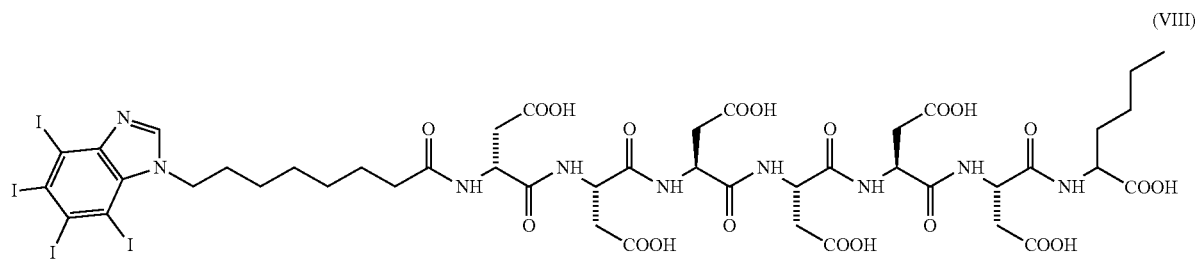
(VIII)
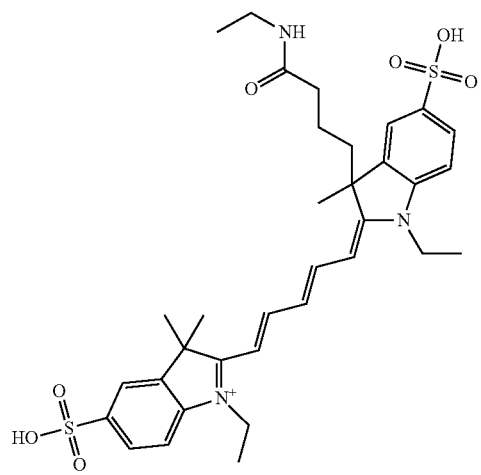
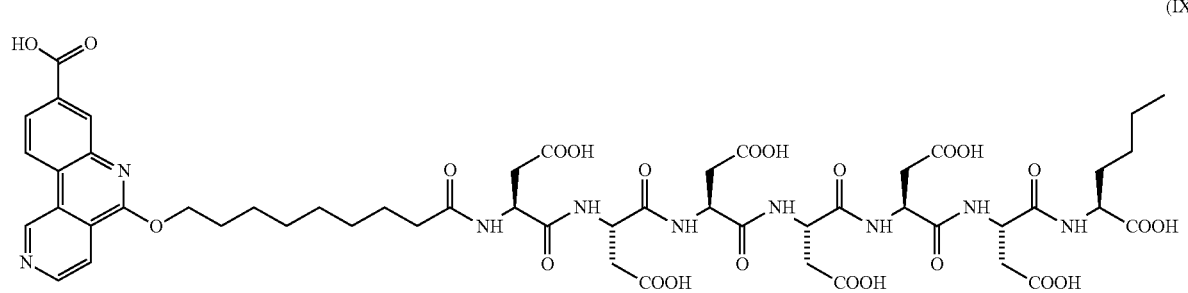
(IX)

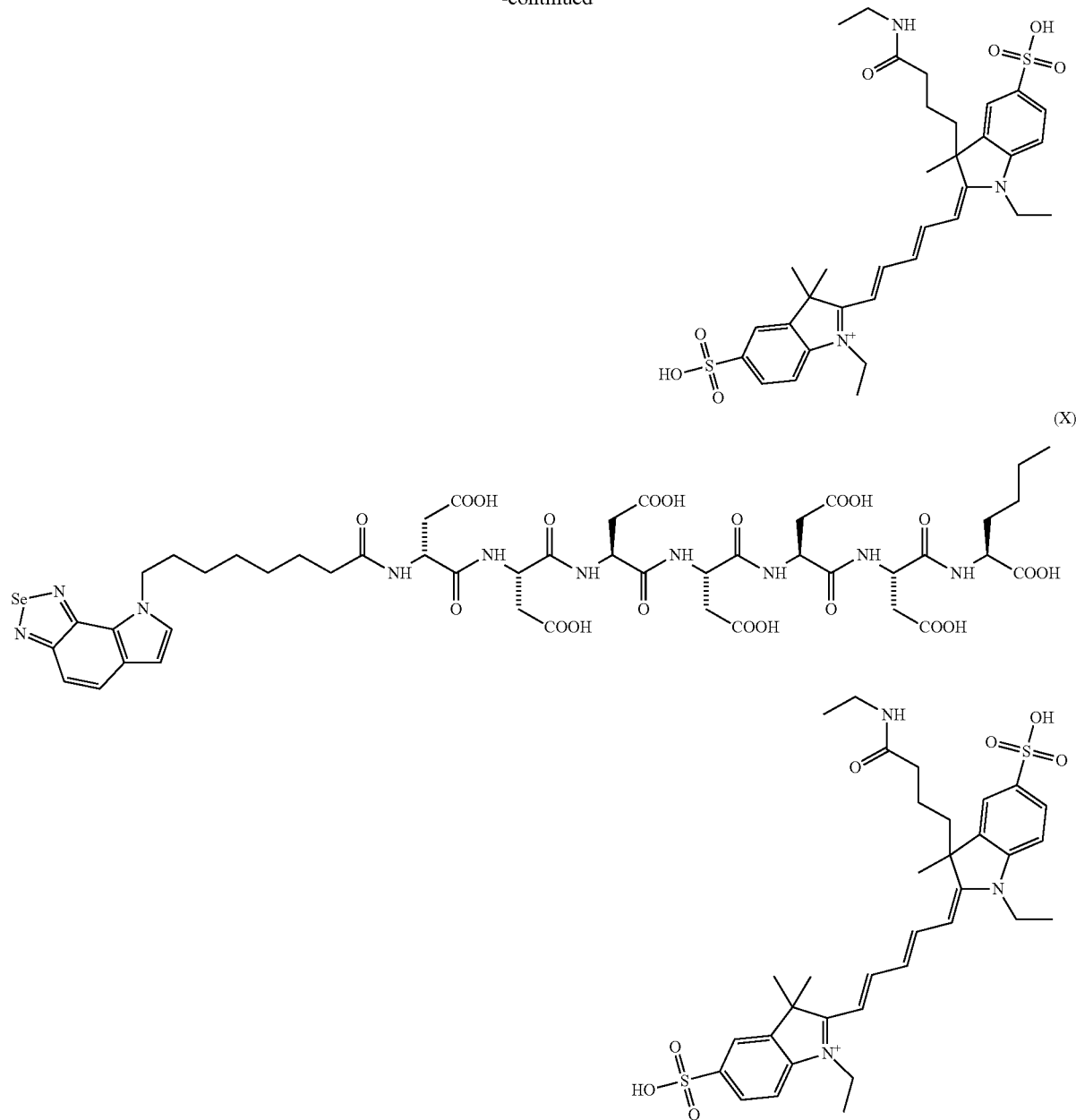

In which the fragment L is lysine; fluorescence label FL is PromoFluor-647 in compounds of formula VI, VIII, IX and X and 5-TAMRA in compound of formula VII; the fragment X is derived from 4,5,6,7-tetrabromo-1H-benzimidazole in compounds of formula VI and VII, from 4,5,6,7-tetraiodo-1H-benzimidazole in compound of formula VIII, from 5-hydroxybenzo[c][2,6]naphthyridine-8-carboxylic acid in compound of formula IX and from 8H-[1,2,5]selenadiazolo[3,4-g]indol in compound of formula X; the fragment Y is derived from octanoic acid in compounds of formula VI, VII, VIII and X, and from nonanoic acid in compound of formula IX; fragment Z is a hexapeptide (D-Asp)-(L-Asp)$_5$ in compounds of formula VI, VII, VIII, and X, and (L-Asp)$_6$ in compound of formula IX.

In the examples of the present invention the fluorescence label is connected via a linker L to the end of fragment Z of the formula I, but fluorescence label may also be attached via a linker L to other moieties in fragment Z.

Figure 4:
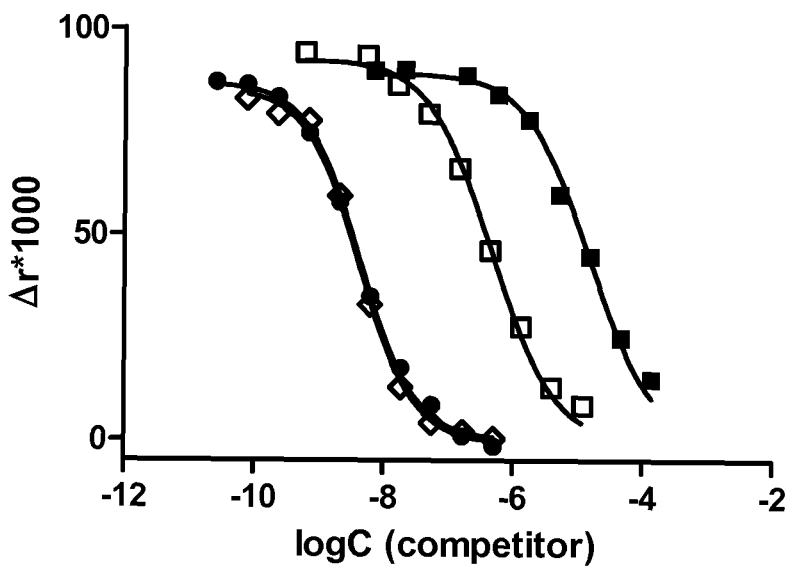
FIG. 4. Dependence of anisotropy change (normalized values) on the concentration of inhibitors CX-4945, non-fluorescent precursor of the probe VI [TBBI-OcA-(D-Asp)-(L-Asp)5-(L-Lys)-OH], TBBI-AcOH and TIBI-AcOH in the presence of constant concentration of CK2α (0.8 nM for TIBI-AcOH and 2 nM for the other compounds) and fluorescent probe VI (0.5 nM for TIBI-AcOH and 3 nM for the other compounds).

The compound of formula VI binds with high affinity to the catalytic subunit (KD=0.4 nM) and to the holoenzyme (KD=0.2 nM) of protein kinase CK2 (FIGS. 1 and 2) and it is displaced from the complex in a competitive manner with the fragment X-Y-Z-L of the same probe, CX-4945, TBBI-AcOH and TIBI-AcOH (FIG. 4). The fragment X-Y-Z-L of the probe of the formula VI binds to protein kinase CK2 very selectively (Example 2), demonstrating the bisubstrate nature of the inhibitor. The selectivity of the inhibitor was tested in a panel of 140 protein kinases, from which more than 50% inhibition at 1 micromolar concentration of the tested inhibitor was observed with 10 kinases. Protein kinase CK2 was inhibited to 1% activity while the activity of the second most inhibited kinase DYRK2 in the same conditions was 17%.

The result points to approximately 20-fold higher affinity of the probe towards CK2 compared to other protein kinases in the panel. Such high selectivity makes it possible to use the fluorescent probe in more complicated systems for the selective detection of protein kinase CK2.

Figure 5:
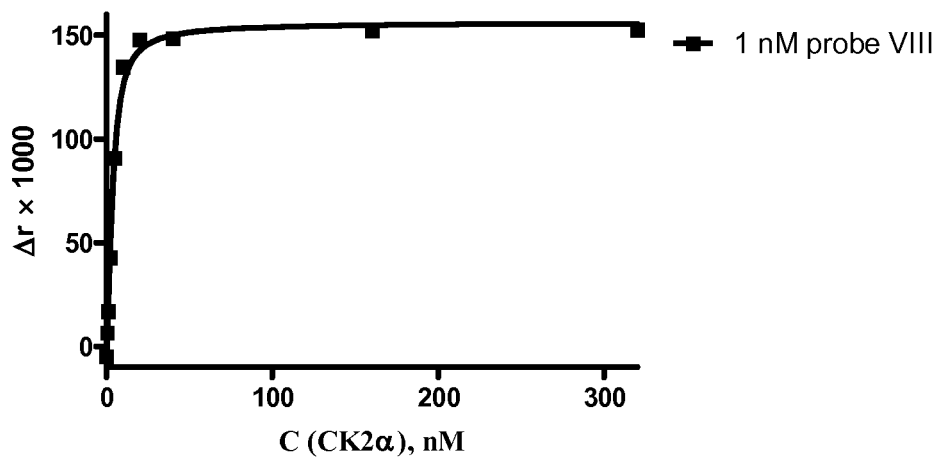
FIG. 5. Titration of the fluorescent probe VIII at 1 nM concentration with CK2α detected by anisotropy change.

The probes of formulas VII and VIII bind to the catalytic subunit of CK2 with high affinity (KD=0.4 nM) demonstrating that the probes can by efficiently used with different fluorescent labels (probes VI and VIII) and different halogeno derivatives of 1H-benzimidazole can be used in the position of fragment X (probe VIII, FIG. 5).

Figure 6:
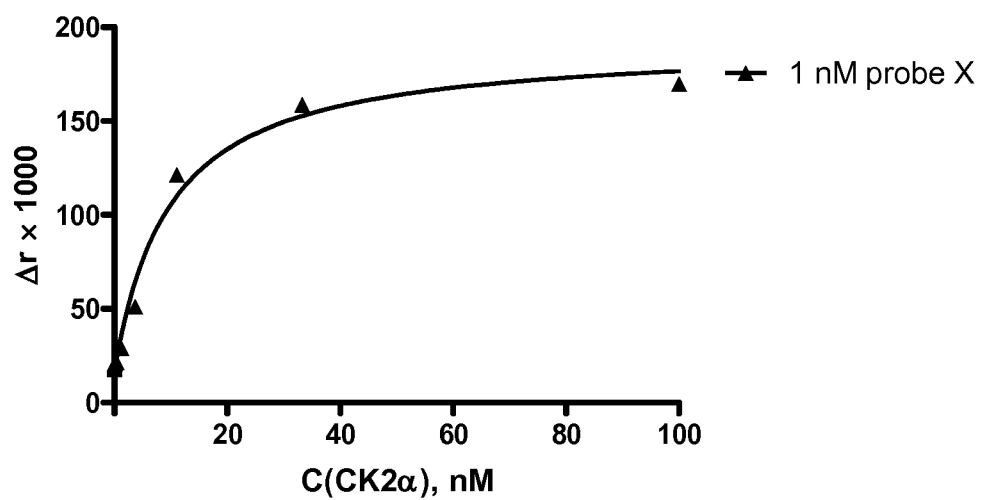
FIG. 6. Titration of the fluorescent probe X at 1 nM concentration with CK2α detected by anisotropy change.
Figure 7:
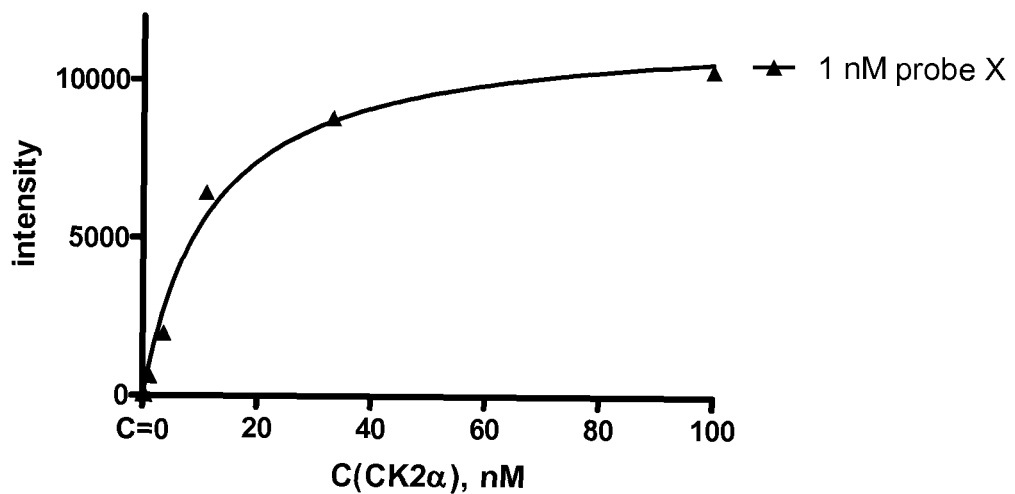
FIG. 7. Titration of the fluorescent probe X at 1 nM concentration with CK2α detected by time gated luminescence intensity measurement (excitation at 337 nm, emission at 675 nm, delay time 50 μs).

The application of selenadiazole-containing heterocycle to the position of fragment X yields a probe of formula X which binds to the catalytic subunit of CK2 with high affinity (KD=10 nM, FIGS. 6 and 7). The binding of this probe to CK2 can be monitored by an intensity change of long-lifetime luminescence signal (FIG. 7) in addition to the change of anisotropy value (FIG. 6) demonstrating that the optimization of the structure of the probe, it is possible to both adjust the affinity and the detection principle for optimization of the probe for different applications.

Figure 8:
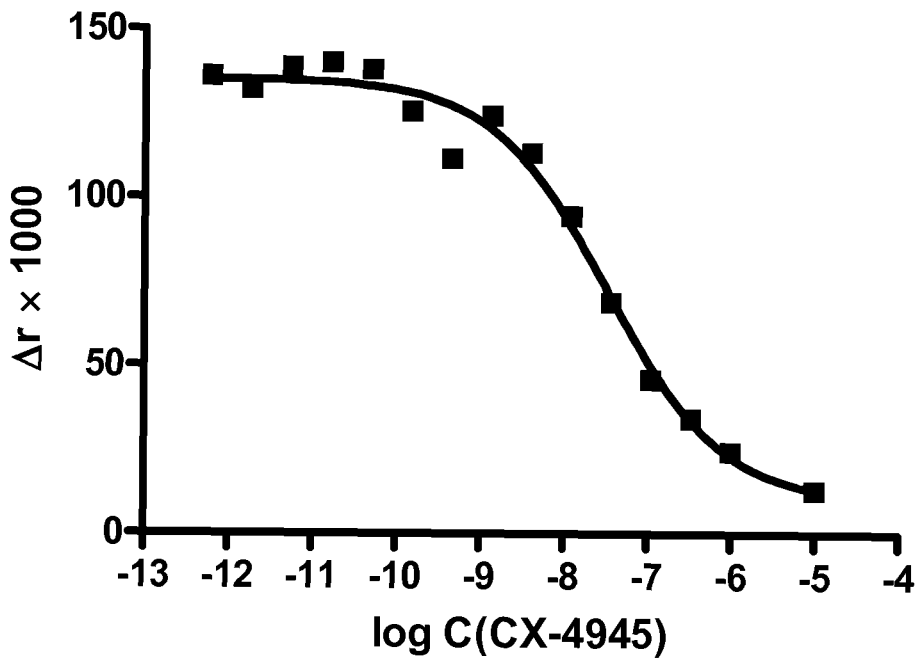
FIG. 8. Dependence of anisotropy change on the concentration of inhibitor CX-4945, in the presence of constant concentration of CK2α (3 nM) and fluorescent probe IX (2 nM).

The probe of formula IX binds to the catalytic subunit of CK2 with very high affinity (KD=0.02 nM, FIG. 8) demonstrating that with structural modifications it is possible to optimize the affinity of the probe for different applications.

The methods for the confirmation of the bisubstrate character of an inhibitor have been highlighted by the authors of the invention in a review paper (Lavogina et al. ChemMedChem. 2010, 5, 23). The fluorescent probes of the present invention can be synthesized by chemical synthesis methods known in the art.

The preferred strategy for the building up of the probe of the general formula I combines solid- and solution-phase synthesis methods. The parts of the molecule X, Y, Z, L and FL can be linked together one by one or as precombined fragments. The strategy of the synthesis of the probe of the general formula I may comprise the following steps:

1. Synthesis of the fragment Z-L on solid phase.
2. Synthesis of the fragment X-Y on solution phase.
3. Coupling of the fragment X-Y to the fragment Z-L on solid phase.
4. Detachment of the obtained fragment X-Y-Z-L from the solid phase.
5. Attachment of the fluorescent label FL to the fragment X-Y-Z-L.

Alternatively, the fragments L and FL may be pre-combined before attachment to the fragment Z and the fragment Y may be attached to the fragment Z separately, followed by the attachment of the fragment X. All reactions can be done in solid phase or in solution phase or in any combination of both.

Detailed description of the synthesis of the probe corresponding to the formula VI is given in the Example 1. The peptide part Z-L of the probe of the formula VI can be synthesized on solid phase according to standard peptide synthesis methods. Preferably, Fmoc-peptide synthesis strategy is used using conventional coupling methods known in the art. The fragment X-Y of the compound of formula VI can be synthesized in solution phase by alkylation of 4,5,6,7-tetrabromo-1H-benzimidazole with appropriately protected bromoalkanoic acid (Scheme 1). After removal of the protecting group by basic hydrolysis, the obtained carboxylic acid is coupled to the peptide part Z-L of the compound using standard amidation reactions (Scheme 2). Alternatively, bromoalkanoic acid may be coupled to the peptide chain Z followed by the attachment of 4,5,6,7-tetrabromo-1H-benzimidazole by alkylation on solid phase. The obtained conjugate may be cleaved from the solid phase and fluorescent label attached in solution phase (Scheme 3) or the attachment of fluorescent label can be done on solid phase.

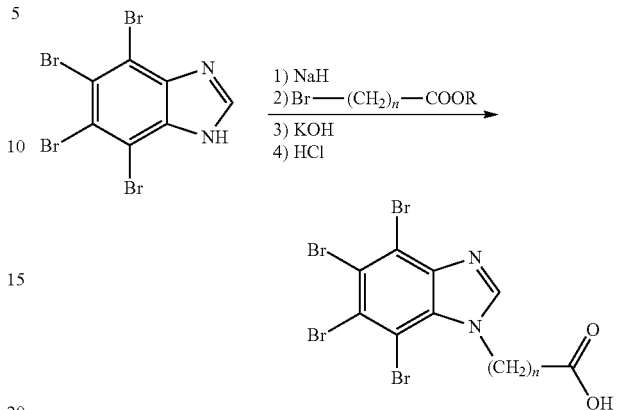

Scheme 1

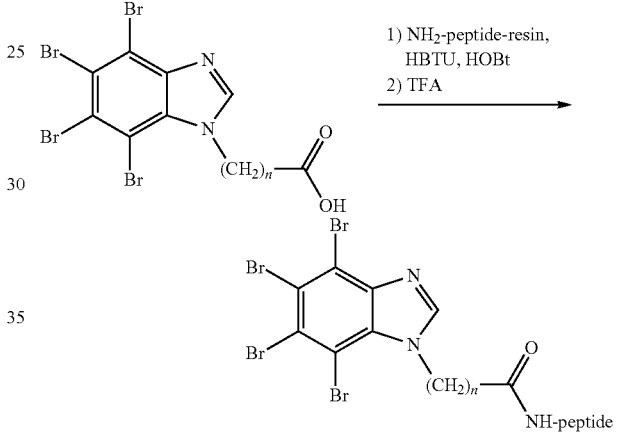

Scheme 2

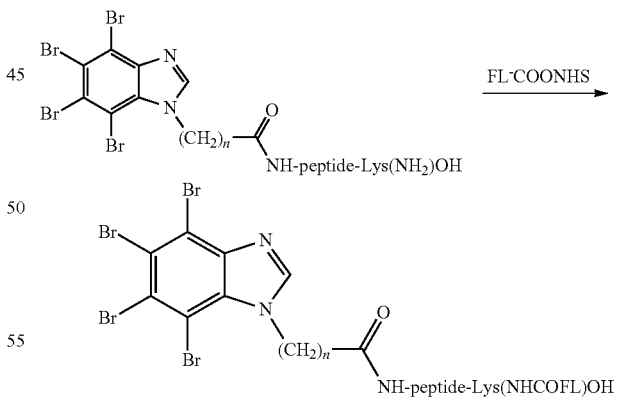

Scheme 3

The compound of formula VIII can be synthesized analogously to the compound of formula VI, starting from 4,5,6,7-tetraiodo-1H-benzimidazole, that can be synthesized according to literature procedures [Gianoncelli et al., Bioorg. Med. Chem. 17 (2009) 7281].

The tricyclic moiety of the fragment X of the compound of formula IX can be synthesized as described previously [Pierre et al., J. Med. Chem. 54 (2011) 635] and alkylated with ethyl ester of 9-bromononanoic acid. After removal of the protecting group by hydrolysis the obtained carboxylic acid (Scheme 4) can be coupled to the peptide fragment of the probe as described for compound of formula VI.

Scheme 4

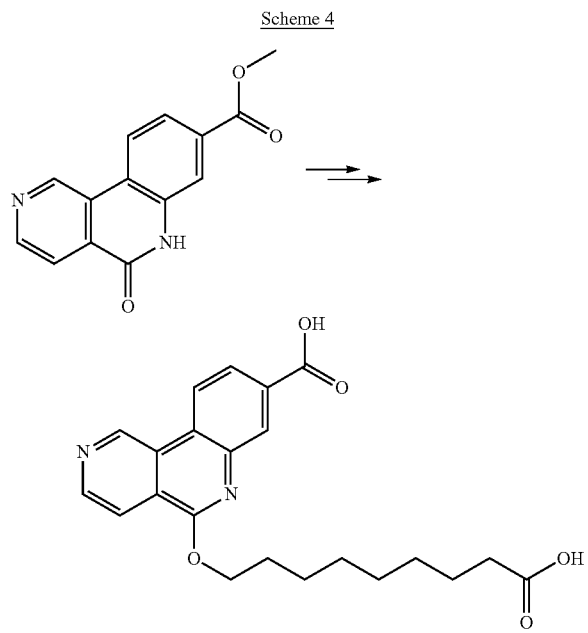

The selenadiazole-containing tricyclic moiety of the compound of formula X can be synthesized as described previously [Edin et al., ARKIVOC (2001) 144] and alkylated with ethyl ester of 8-bromooctanoic acid analogously to the synthesis of compound of formula VI (Scheme 5). The hydrolysis of the obtained ester yields the corresponding carboxylic acid that can be coupled to the peptide chain using standard peptide synthesis methods known in the art as described for compound of formula VI.

The final purification of the probes can be carried out by HPLC using standard ACN-water gradient solvent systems well known in the art.

Scheme 5

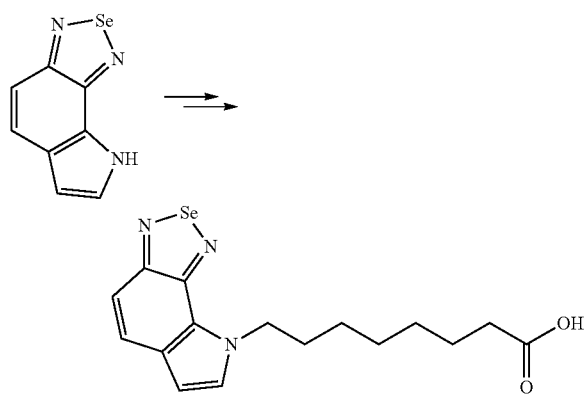

Assay Formats Utilizing the Fluorescent Probes.

The fluorescent probes of the invention change fluorescence properties (intensity, anisotropy) upon binding to the catalytic site of protein kinase CK2 and can be used for the monitoring of the equilibrium between the probe in free and bound state. The detected parameter responsive to the binding reaction is preferably fluorescence polarization (or fluorescence anisotropy), but other properties can be detected such as fluorescence intensity, fluorescence intensity distribution, fluorescence correlation, fluorescence resonance energy transfer and fluorescence lifetime. These methods are well characterized in the literature [e.g., White et al. Adv. Drug Deliv. Rev. 57 (2005) 17] and are known to people skilled in the art.

Fluorescence polarization assay is based on the measurement of the change in rotational speed of a fluorescence ligand during its excited lifetime upon binding to its receptor. Excitation of the solution of a fluorescent probe with plane polarized light causes photoselection since the probability of absorption is dependent on the angle between the excitation dipole moment of the fluorophore and the plane of polarization of exciting light. The emitted light will be depolarized because the fluorophores rotate during the lifetime of the excited state. The extent of depolarization is dependent on the volume of the rotating particles. The measured polarization value for the fluorescent probe free in the solution will be smaller than the polarization value for the probe bound to protein.

The fluorescence polarization assay can thus be used for the detection of the interaction between small-molecule fluorescent probes and larger molecules. Both terms, fluorescence polarization and fluorescence anisotropy describe the same phenomenon and can be used interchangeably. Due to mathematical simplicity, anisotropy values are preferred.

Fluorescence polarization assay is homogeneous and as such does not require separation steps like chromatography, gel filtration, centrifugation, precipitation or electrophoresis. Since the measurement of polarization is ratiometric, the assay is well suited to miniaturization and can be performed equally well in microplates or in cuvettes. In the examples of the present invention, the assays are performed in 20 μL volumes in 384-well non-binding surface microplates and the fluorescence anisotropy was measured with PHERAstar fluorescence plate reader (BMG Labtech). The degree of polarization is determined by measuring the fluorescence intensities of the emitted light in parallel and in perpendicular planes in respect to the polarization plane of exciting light. In one embodiment of the fluorescent probe of the invention, the compound of formula VI has molecular mass of 2 kDa. The molecular mass of the catalytic subunit of CK2 is ca 40 kDa, resulting in an increase of fluorescence anisotropy value by 0.15 units upon the complex formation.

The assays can be performed with native isoforms of protein kinase CK2 as well as chemically, enzymatically and genetically modified versions of the isoforms of protein kinase CK2, including mutated, labeled, fused and truncated forms incorporating the catalytic domain.

The optimization of the conditions for the assay can be readily performed by one skilled in the art and it involves the following:

1. the choice of fluorescence dye that must have sufficient brightness to yield measurable signal with the used detection system at the concentration used in the assay and have minimal interference with the binding of the probe to the kinase,
2. The choice of excitation and emission wavelengths that must be suitable for the chosen fluorescence dye,
3. The assay volume that must be optimal to afford stable mixing and measurements and minimize consumption of the materials,
4. The buffer composition and microplate material that must minimize non-specific adsorption of the samples to the walls of the wells of the microplate,
5. The buffer composition, pH and temperature that must be suitable for the kinase used in the assay.
6. The concentrations of the probe and the kinase that must yield measurable change of the signal in response to the changed parameter in the assay,
7. The incubation time of the assay solutions before measurements that must reach equilibrium between the assay components and avoid the concentration change of the components due to evaporation or degradation.

Detection and Quantification of the Active Form of Protein Kinase.

The knowledge about the amount of active kinase is important in many applications such as the determination of the inhibitory potencies of tight binding inhibitors or determination of the activity of the kinase in biological fluids. Nonselective methods for the determination of the total content of protein in a sample (Bradford, Lowry, SDS electrophoresis) do not distinguish protein kinases in their active and inactive states. The fluorescent probes of the present invention bind to the active form of protein kinase CK2 and can be used for its quantification. An assay for the quantification of the active form of protein kinase CK2 comprises the following steps:
1. Estimation of the KD-value of the complex between the probe and protein kinase.
2. Contacting the fluorescent probe at a final concentration higher than the KD-value with a series of samples of the kinase with unknown activity at different dilutions and measuring the fluorescence signals of the formed complex in the samples.
3. Calculating the fraction of the active form of the kinase.

Once the $K_D$-value for the fluorescent probe is known only steps 2 and 3 have to be performed. The fraction of the active form of the kinase can be calculated from anisotropy data by nonlinear regression analysis according to the relationship:

$$A = A_f(1-X_1) + A_b X_1,$$

where $$X_1 = QX_2/[1+X_2(Q-1)],$$

where $$X_2 = \{P + KD + kE_0 - [(P+KD+kE_0)^2 - 4PkE_0]^{1/2}\}/2P,$$

where A is measured anisotropy, $A_f$ is the anisotropy of free probe, $A_b$ is the anisotropy of the probe-kinase complex, Q is the ratio of fluorescence quantum yield of the probe-kinase complex and the free probe, P is the concentration of the fluorescent probe, $E_0$ is the nominal concentration of kinase, k is the fraction of active kinase in enzyme preparation and KD is the dissociation constant of the probe-kinase complex.

An example of this assay is given in examples 3-5.

A good correlation between the fraction of the enzyme binding to the probes and its catalytic activity was observed which proves that the probes can bind to the catalytically active form of the kinase.

Competition Assay.

An assay that utilizes the probes of the present invention for the detection and characterization of inhibitors of protein kinase CK2 comprises the following steps:
1. establishing the KD or the complex of the fluorescent probe with the kinase;
2. contacting the fluorescent probe with the kinase and measuring the fluorescence signal of the formed complex;
3. incubating of the complex formed in the previous step with a series of different concentrations of the inhibitory compound and measuring of the
4. fluorescence signal at each concentration of the inhibitor;
5. calculating of the $K_d$ of the inhibitory compound for its binding to the active site of the kinase proceeding from the KD for the complex of the fluorescent probe with the kinase and the results of the measurements of the step III.

Once the $K_D$-value for the fluorescent probe is known, only steps 2-4 have to be performed.

The dissociation constants for the complexes between protein kinase CK2 and screened compounds ($K_d$ values) can be calculated according to the relationship [Nikolovska-Coleska et al., Anal. Biochem. 332 (2004) 261]:

$$K_d = I50/(L_{50}/KD + P_0/KD + 1),$$

where $K_d$ is the dissociation constant of the kinase-inhibitor complex, KD is the dissociation constant of the kinase-probe complex, $I_{50}$ is the concentration of the free inhibitor at 50% inhibition, $L_{50}$ is the concentration of the free probe at 50% inhibition and $P_0$ is the concentration of the free enzyme at 0% inhibition.

Examples of the application of the assay for the characterization of inhibitors of protein kinase CK2 are presented in example 6.

Due to the bisubstrate character of the kinase-binding fragment, the probes can be displaced in competitive manner from the complex with protein kinase with inhibitors targeted to the peptide/protein binding region or the nucleotide binding pocket of the catalytic subunit of the enzyme or both. The fluorescent probes of the invention make it possible to detect both types of inhibitors in a single assay format. Differently from the ATP-competitive probes the probes of the present invention enable the testing of interactions of CK2α with other proteins that could be very important for screening and characterization of proteins that regulate the activity and localization of CK2α.

Due to the high affinity of the probes (KD<10 nM) and high brightness of the fluorescence labels the concentration of the probes in an assay may be in less than nanomolar range that makes it possible to precisely determine the binding constants for high-affinity inhibitors [e.g., CX-4945, $K_d$ determined with the described assay is 0.3 nM, which is equal to the value reported in literature 0.4 nM, Siddiqui-Jain et al., Cancer Res. 70 (2010) 24 10288].

Experimental Part

Abbreviations

ACN—acetonitrile;
Asp—aspartic acid;
BOC—tert-butoxycarbonyl;
DMF—N,N-dimethylformamide;
DMSO—dimethylsulfoxide;
DTT—dithiothreitol;
EDTA—ethylenediaminetetraacetic acid;
ESI—electrospray ionization;
Fmoc—9-fluorenylmethyloxycarbonyl;
HEPES—2-[4-(2-hydroxyethyl)piperazin-1-yl]ethane-sulfonic acid;
HBTU—O-benzotriazole-N,N,N',N'-tetramethyluronium hexafluorophosphate;
HOBt—1-hydroxybenzotriazole;
HPLC—high performance liquid chromatography;
HRMS—high resolution mass spectrometry;
Lys—lysine;
NHS—N-hydroxysuccinimide;
NMR—nuclear magnetic resonance;
OcA—octanoic acid;
TBBI—4,5,6,7-tetrabromo-1H-benzimidazole;
TIBI—4,5,6,7-tetraiodo-1H-benzimidazole;
TFA—trifluoroacetic acid;

EXAMPLES

Example 1

The Synthesis of the Bisubstrate Fluorescent Probes VI-X
A. Synthesis of 8-(4,5,6,7-tetrabromo-1H-benzimidazole-1-yl)octanoic acid (TBBI-OcA)
4,5,6,7-tetrabromo-1H-benzimidazole (115 mg, 0.26 mmol) and NaH suspension (12 mg, ~0.28 mmol) were stirred in DMF for 30 min and then 8-bromooctanoic acid methyl ester (182 mg, 0.77 mmol) was added. The solution was stirred for 2 days and then evaporated to dryness. The residue was purified by flash chromatography (CHCl$_3$: methanol; 20:1 by volume). The methyl ester was hydrolyzed in the mixture of methanol and aqueous KOH for 1 hour and the solvents were removed in vacuum. The obtained residue was partitioned between ethyl acetate and KHSO$_4$, the organic layer was dried and evaporated to yield 8-(4,5,6,7-tetrabromo-1H-benzimidazole-1-yl)octanoic acid (95 mg, 62% over two steps). $^1$H NMR (200 MHz; DMSO$_{6d}$; Me$_4$Si) 1.28 (m, 6H), 1.48 (m, 2H), 1.76 (m, 2H), 2.19 (t, J=7.3 Hz, 2H), 4.48 (t, J=7.6 Hz, 2H), 8.51 (s, 1H), 11.91 (br, 1H). $^{13}$C NMR (50 MHz; DMSO$_{6d}$; Me$_4$Si) 24.3, 25.5, 28.1, 28.3, 31.5, 33.6, 46.4, 106.5, 116.6, 120.4, 122.3, 131.3, 143.7, 148.9, 174.4.

B. Synthesis of TBBI-OcA-(D-Asp)-(L-Asp)5-(L-Lys)-OH

TBBI-OcA-(D-Asp)-(L-Asp)5-(L-Lys)-OH was prepared by using traditional Fmoc solid-phase peptide synthesis methods on Fmoc-Lys(BOC)-Wang resin. Tert-butyl ester-protected aspartic acids (3 equivalents) were preactivated for 3 minutes with HOBt/HBTU (2.94 equivalents each) and N-methylmorpholine (9 equivalents) in DMF and the resin was treated with the coupling solutions for 40-60 min. The completeness of each step was monitored with Kaiser-test, which was followed by removal of Fmoc group by 20% piperidine solution in DMF (20 min). The coupling of TBBI-OcA to the peptides was carried out with 1.5 eq of the acid activated with HOBt/HBTU (1.47 equivalents each) and N-methylmorpholine (9 equivalents) in DMF for 3 h. The protection groups were removed and the conjugate cleaved from the resin with 2 h treatment with 90% trifluoroacetic acid (5% triisopropylsilane, 5% water). The conjugate was purified with C18 reversed phase HPLC (ACN/0.1% TFA gradient) and lyophilized. ESI m/z: calculated for [M+H]$^+$ 1395. found 1395. [M+H]$^{2+}$ 698. found 698.

C. Synthesis of Probes of Formulas VI and VII)

TBBI-OcA-(D-Asp)-(L-Asp)5-(L-Lys)-OH was labeled with PromoFluor-647 at the side-chain of lysine in a mixture of NHS-activated fluorescence label (1.2 eq), triethylamine (10-50 eq) in DMF, 3 h at rt. The solvent was removed in vacuo, the product was purified by HPLC (ACN/0.1% TFA gradient) and lyophilized. ESI HRMS m/z: calculated [M+2H]$^{2+}$ 1008.13160. found 1008.13173 (monoisotopic mass). The probe VII was synthesized by the same protocol using 5-TAMRA NHS-ester as the activated fluorescent dye.

D. Synthesis of the Probe of Formula VIII 4,5,6,7-tetraiodo-1H-benzimidazole was synthesized according to literature procedures [Gianoncelli et al., Bioorg. Med. Chem. 17 (2009) 7281] in 55% yield and it was alkylated with 8-bromooctanoic acid isopropyl ester using potassium carbonate as the base in DMF. The hydrolysis of the ester yielded the carboxylic acid that was coupled with the peptide chain on solid phase using the same conditions as described for the probe of formula VI. The probe was labeled with fluorescent dye PromoFLuor-647 as described for probe VI and purified with HPLC.

E. Synthesis of the Probe of Formula IX

The tricyclic moiety methyl 5-oxo-5,6-dihydrobenzo[c][2,6]naphthyridine-8-carboxylate was synthesized as described in literature [Pierre et al., J. Med. Chem. 54 (2011) 635] and alkylated with ethyl ester of 9-bromononanoic acid in the presence of NaH. Hydrolysis of the ester gave carboxylic acid derivative that was coupled to the peptide on Wang resin. The peptide conjugate was cleaved from the resin with TFA, the obtained regioisomers were separated by HPLC and labeled with PromoFluor-647 as described for probe VI to yield the probe IX.

F. Synthesis of the Probe X

The selenadiazole-containing moiety was synthesized by literature procedures in 15% yield [Edin et al., ARKIVOC (2001) 144] and alkylated with ethyl ester of 8-bromooctanoic acid in the presence of NaH. Hydrolysis of the ester gave carboxylic acid derivative that was coupled to the peptide on Wang resin. The peptide conjugate was cleaved from the resin with TFA, the obtained compound was purified by HPLC and labeled with PromoFluor-647 as described for probe VI to yield the probe of formula X.

Example 2

Selectivity of Inhibition of the Compound TBBI-OcA-(D-Asp)-(L-Asp)5-(L-Lys)-OH (Precursor of Probe VI)

The selectivity of inhibition of compound TBBI-OcA-(D-Asp)-(L-Asp)5-(L-Lys)-OH was tested in a panel of 140 protein kinases. The results of the testing are expressed as residual activity percent of the kinases in the presence of the compound TBBI-OcA-(D-Asp)-(L-Asp)5-(L-Lys)-OH at 1 micromolar concentration.

| Residual activities of protein kinases in the presence of bisubstrate inhibitor TBBI-OcA-(D-Asp)-(L-Asp)$_5$-(L-Lys)-OH | |
|---|---|
| Protein kinase | Residual activity (%) |
| CK2 | 1 (±0) |
| DYRK2 | 17 (±1) |
| PLK1 | 18 (±3) |
| CLK2 | 24 (±2) |
| ERK8 | 25 (±0) |
| DYRK3 | 30 (±2) |
| DYRK1A | 36 (±3) |
| HIPK2 | 36 (±1) |
| GSK3b | 46 (±7) |
| CK1δ | 49 (±5) |
| TTK | 52 (±21) |
| IRR | 55 (±20) |
| IKKb | 55 (±6) |
| Src | 57 (±3) |
| NUAK1 | 58 (±13) |
| PIM3 | 59 (±3) |
| SRPK1 | 61 (±11) |
| Lck | 62 (±4) |
| TAK1 | 62 (±3) |
| S6K1 | 62 (±10) |
| PIM1 | 62 (±10) |
| CDK2-Cyclin A | 64 (±2) |
| CDK9-Cyclin T1 | 65 (±19) |
| MARK2 | 66 (±3) |
| JAK2 | 66 (±3) |
| MKK2 | 66 (±0) |
| HIPK1 | 68 (±9) |
| AMPK | 69 (±1) |
| MAPKAP-K3 | 69 (±20) |
| IR | 70 (±7) |
| RSK2 | 70 (±1) |
| CK1γ2 | 71 (±5) |
| PAK4 | 71 (±3) |
| EIF2AK3 | 71 (±1) |
| PKBb | 72 (±5) |
| PKD1 | 72 (±7) |
| MARK3 | 73 (±11) |
| PKBa | 73 (±22) |
| SIK2 | 74 (±7) |
| PRAK | 74 (±5) |
| SIK3 | 74 (±3) |
| HIPK3 | 75 (±0) |
| MARK4 | 75 (±8) |
| BRSK2 | 75 (±4) |
| VEG-FR | 76 (±4) |
| AMPK (hum) | 76 (±2) |
| PDGFRA | 77 (±4) |
| EPH-A2 | 80 (±5) |
| EF2K | 80 (±8) |
| BTK | 80 (±4) |
| PAK5 | 81 (±10) |
| TESK1 | 81 (±4) |
| MKK6 | 82 (±2) |

Residual activities of protein kinases in the presence of
bisubstrate inhibitor TBBI-OcA-(D-Asp)-(L-Asp)₅-(L-Lys)-OH

| Protein kinase | Residual activity (%) |
|---|---|
| MARK1 | 83 (±6) |
| DAPK1 | 84 (±11) |
| IKKe | 84 (±7) |
| TAO1 | 84 (±8) |
| JNK3 | 85 (±11) |
| PDK1 | 86 (±20) |
| TSSK1 | 86 (±11) |
| PAK6 | 86 (±11) |
| MAP4K3 | 86 (±17) |
| WNK1 | 88 (±1) |
| RSK1 | 88 (±0) |
| MNK2 | 89 (±22) |
| MAPKAP-K2 | 89 (±11) |
| IRAK1 | 89 (±2) |
| MLK3 | 89 (±3) |
| TTBK1 | 90 (±2) |
| ROCK 2 | 91 (±5) |
| CAMKKb | 91 (±6) |
| MELK | 92 (±1) |
| CSK | 92 (±5) |
| ERK2 | 92 (±6) |
| PRK2 | 92 (±4) |
| PIM2 | 92 (±0) |
| TBK1 | 93 (±9) |
| p38d MAPK | 93 (±6) |
| NEK2a | 94 (±7) |
| PKCa | 94 (±10) |
| MEKK1 | 95 (±13) |
| BRSK1 | 95 (±3) |
| TTBK2 | 95 (±6) |
| GCK | 95 (±13) |
| SmMLCK | 96 (±1) |
| MPSK1 | 96 (±2) |
| STK33 | 96 (±4) |
| LKB1 | 96 (±15) |
| p38g MAPK | 97 (±10) |
| ZAP70 | 97 (±4) |
| EPH-B3 | 98 (±10) |
| TGFBR1 | 98 (±4) |
| ERK5 | 98 (±8) |
| MNK1 | 99 (±11) |
| MST2 | 99 (±7) |
| SYK | 100 (±3) |
| MST3 | 100 (±3) |
| PKA | 100 (±2) |
| Aurora B | 100 (±19) |
| MKK1 | 101 (±9) |
| ABL | 101 (±26) |
| CHK2 | 101 (±6) |
| PAK2 | 102 (±4) |
| EPH-B1 | 102 (±11) |
| MSK1 | 102 (±8) |
| JNK1 | 103 (±6) |
| YES1 | 103 (±21) |
| HER4 | 103 (±5) |
| EPH-B4 | 104 (±9) |
| PHK | 105 (±8) |
| PKCz | 105 (±7) |
| TIE2 | 105 (±13) |
| JNK2 | 105 (±5) |
| CAMK1 | 105 (±3) |
| PKCγ | 106 (±8) |
| TLK1 | 107 (±3) |
| DDR2 | 109 (±6) |
| FGF-R1 | 110 (±7) |
| ERK1 | 110 (±9) |
| ULK2 | 110 (±2) |
| TrkA | 111 (±15) |
| ULK1 | 111 (±25) |
| MLK1 | 112 (±7) |
| BRK | 113 (±8) |
| EPH-B2 | 113 (±11) |
| MST4 | 114 (±20) |
| ASK1 | 114 (±34) |
| p38a MAPK | 116 (±11) |
| IGF-1R | 116 (±16) |
| EPH-A4 | 117 (±5) |
| IRAK4 | 118 (±16) |
| Aurora A | 118 (±0) |
| RIPK2 | 120 (±3) |
| NEK6 | 121 (±9) |
| p38b MAPK | 122 (±1) |
| SGK1 | 127 (±0) |
| OSR1 | 130 (±50) |
| MAP4K5 | 132 (±14) |
| CHK1 | 134 (±14) |
| MINK1 | 139 (±18) |

Example 3

Characterization of the Complex Between the Fluorescent Probe of Formula VI and the Catalytic Subunit of Protein Kinase CK2

The binding of the fluorescent probe of formula VI to the catalytic subunit of protein kinase CK2 (CK2α) was studied at 0.2 nM concentration of the probe and 2-fold dilutions of CK2α in a buffer containing 50 mM HEPES (pH 7.5), 150 mM NaCl, 5 mM DTT, 0.1 mM EDTA and 0.005% tween 20 in 20 μl volumes in 384-well microplate. The microplate was incubated at 30° C. for 10 min and fluorescence anisotropy was measured with excitation at 590 nm (50 nm bandpass filter) and emission at 675 nm (50 nm bandpass filter). The change in fluorescence anisotropy vs kinase concentration was plotted and KD value was calculated by the application of nonlinear regression analysis to the relationship:

$$A = A_f(1-X_1) + A_b X_1,$$

where $$X_1 = QX_2/[1+X_2(Q-1)],$$

where $$X_2 = \{P + KD + kE_0 - [(P+KD+kE_0)^2 - 4PkE_0]^{1/2}\}/2P$$

where A is measured anisotropy, $A_f$ is the anisotropy of free probe, $A_b$ is the anisotropy of the probe-CK2α complex, Q is the ratio of fluorescence quantum yield of the probe-CK2α complex and the free probe, P is the concentration of the fluorescent probe, $E_0$ is the nominal concentration of the kinase, k is the fraction of active kinase in enzyme preparation and KD is the dissociation constant of the probe-CK2α complex. Q value of 1.1 was calculated by dividing the total fluorescence intensity of the complex with the total fluorescence intensity of the free probe. The KD-value or 0.4 nM was calculated by nonlinear regression analysis for the probe-CK2α complex (FIG. 1).

Example 4

Characterization of the Complex Between the Fluorescent Probe of Formula VI and the Holoenzyme of Protein Kinase CK2

The binding of the fluorescent probe to the holoenzyme of protein kinase CK2 was studied at 0.2 nM concentration of the probe, 2-fold dilutions of CK2α and 100 nM regulatory subunit of CK2 (CK2β) in a buffer containing 50 mM HEPES (pH 7.5), 150 mM NaCl, 5 mM DTT, 0.1 mM EDTA and 0.005% tween 20 in 20 μl volumes in 384-well microplate.

Figure 2:
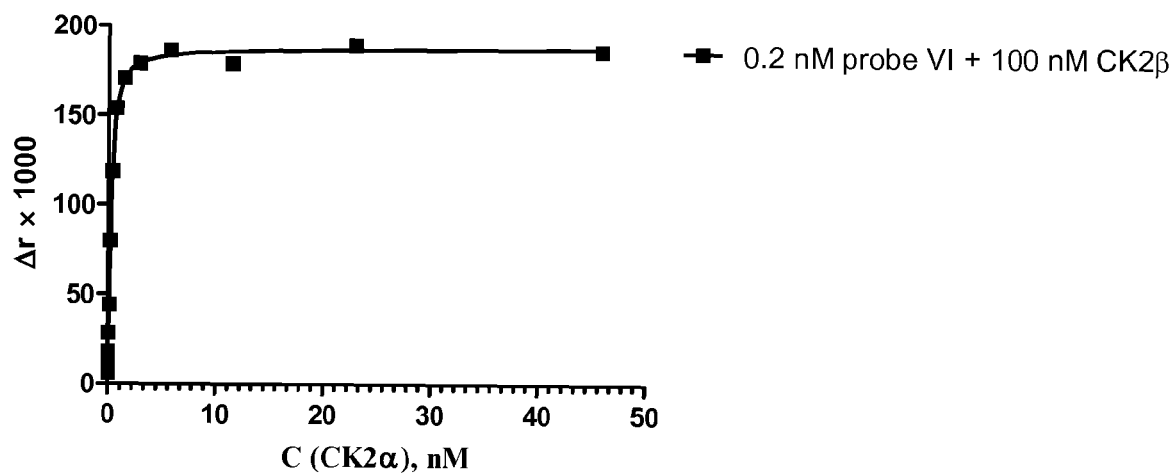
FIG. 2. Titration of the fluorescent probe VI at 0.2 nM concentration with CK2 holoenzyme (2-fold dilutions of CK2α in the presence of 100 nM CK2β) detected by anisotropy change.

The microplate was incubated at 30° C. for 10 min and fluorescence anisotropy was measured with excitation at 590 nm (50 nm bandpass filter) and emission at 675 nm (50 nm bandpass filter). The change in fluorescence anisotropy vs kinase concentration was plotted and KD-value was calculated by the application of nonlinear regression analysis to the relationship:

$$A = A_f(1-X_1) + A_b X_1,$$

where $$X_1 = QX_2/[1+X_2(Q-1)],$$

where $$X_2 = \{P+KD+kE_0 - [(P+KD+kE_0)^2 - 4PkE_0]^{1/2}\}/2P$$

where A is measured anisotropy, $A_f$ is the anisotropy of free probe, $A_b$ is the anisotropy of the probe-CK2 holoenzyme complex, Q is the ratio of fluorescence quantum yield of the probe-CK2 holoenzyme complex and the free probe, P is the concentration of the fluorescent probe, $E_0$ is the nominal concentration of CK2α, k is the fraction of active kinase in enzyme preparation and $K_D$ is the dissociation constant of the probe-CK2 holoenzyme complex. KD-value of 0.2 nM was calculated for the probe-CK2 holoenzyme complex (FIG. 2).

Example 5

Determination of the Concentration of the Active Form of the Catalytic Subunit of CK2

Figure 3:
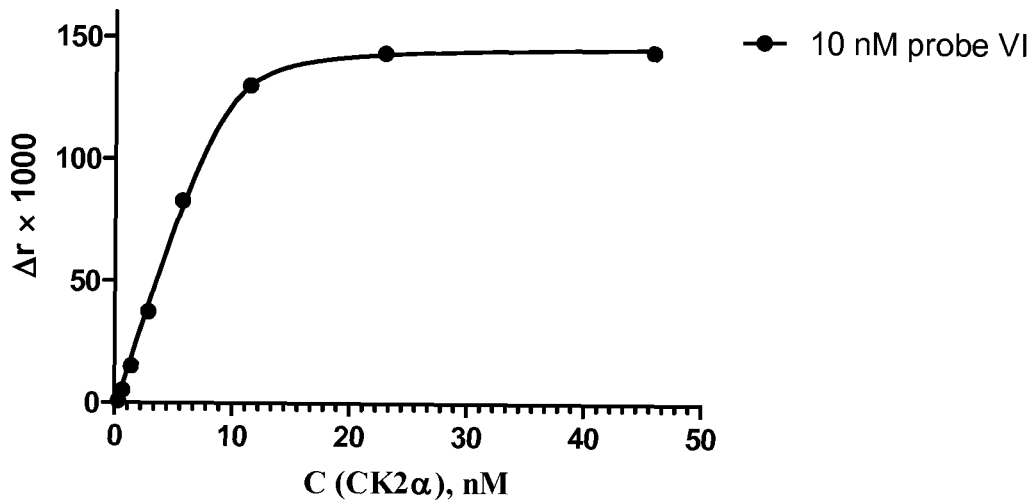
FIG. 3. Titration of the fluorescent probe VI at 10 nM concentration with CK2α detected by anisotropy change.

The concentration of the active form of the catalytic subunit of CK2 (CK2α) was measured at 10 nM concentration of the probe or formula VI and 2-fold dilutions of CK2α in a buffer containing 50 mM HEPES (pH 7.5), 150 mM NaCl, 5 mM DTT, 0.1 mM EDTA and 0.005% tween 20 in 20 μl volumes in 384-well microplate. The microplate was incubated at 30° C. for 10 min and fluorescence anisotropy was measured with excitation at 590 nm (50 nm bandpass filter) and emission at 675 nm (50 nm bandpass filter). The change in fluorescence anisotropy vs kinase concentration was plotted and the fraction of the active form or the kinase, k, was calculated by the application of nonlinear regression analysis to the relationship:

$$A = A_f(1-X_1) + A_b X_1,$$

where $$X_1 = QX_2/[1+X_2(Q-1)]$$

where $$X_2 = \{P+KD+kE_0 - [(P+KD+kE_0)^2 - 4PkE_0]^{1/2}\}/2P$$

where A is measured anisotropy, $A_f$ is the anisotropy of free probe, $A_b$ is the anisotropy of the probe-CK2 holoenzyme complex, Q is the ratio of fluorescence quantum yield of the probe-CK2 holoenzyme complex and the free probe, P is the concentration of the fluorescent probe, $E_0$ is the nominal concentration of CK2α, k is the fraction of active kinase in enzyme preparation and KD is the dissociation constant of the probe-CK2 holoenzyme complex. The obtained value of 0.3 shows that 30% of the nominal kinase is in the active form in this sample of CK2α (FIG. 3).

Example 6

Competition Experiments for Determination of the Binding Constants of Inhibitors of CK2

Different compounds were screened for binding to the active site of protein kinase CK2 against fixed concentrations of fluorescent probe of formula VI and catalytic subunit of CK2 (CK2α) in a buffer containing 50 mM HEPES (pH 7.5), 150 mM NaCl, 5 mM DTT, 0.1 mM EDTA and 0.005% tween 20 in 20 μl volumes in 384-well microplate. The microplate was incubated at 30° C. for 10 min and fluorescence anisotropy was measured with excitation at 590 nm (50 nm bandpass filter) and emission at 675 nm (50 nm bandpass filter). The following $IC_{50}$ values were obtained for inhibitors (FIG. 4):

| Screened compound | $IC_{50}$ | $K_d$ |
|---|---|---|
| CX-4945 | 4.4 nM | 0.3 nM |
| TBBI-OcA-(D-Asp)-(L-Asp)$_5$-(L-Lys)-OH | 4.3 nM | 0.3 nM |
| TIBI-AcOH | 390 nM | 122 nM |
| TBBI-AcOH | 11.5 μM | 1.5 μM |

The dissociation constants for the complexes between protein kinase CK2 and screened compounds (Kd-values) were calculated according to the relationship [Nikolovska-Coleska et al., Anal. Biochem. 332 (2004) 261]:

$$K_d = I_{50}/(L_{50}/KD + P_0/KD + 1),$$

where $K_d$ is the dissociation constant of the kinase-inhibitor complex, KD is the dissociation constant of the kinase-probe complex, $I_{50}$ is the concentration of the free inhibitor at 50% inhibition, $L_{50}$ is the concentration of the free probe at 50% inhibition and $P_0$ is the concentration of the free enzyme at 0% inhibition.

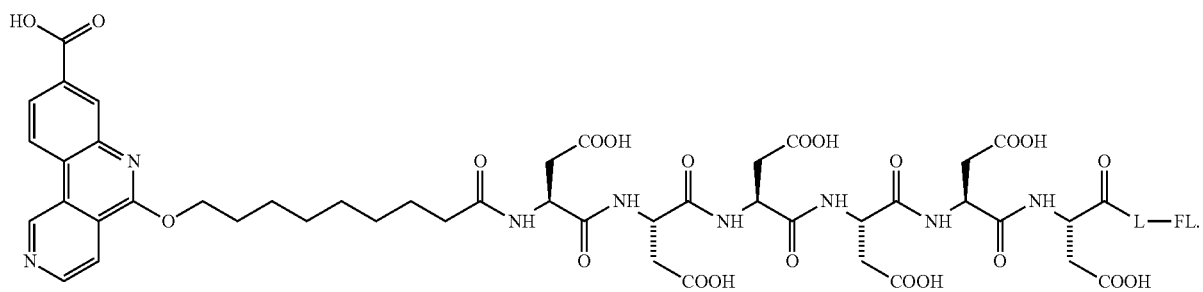

12. The bisubstrate fluorescent probe of claim 1, wherein the structure of the probe is selected from the group consisting of:
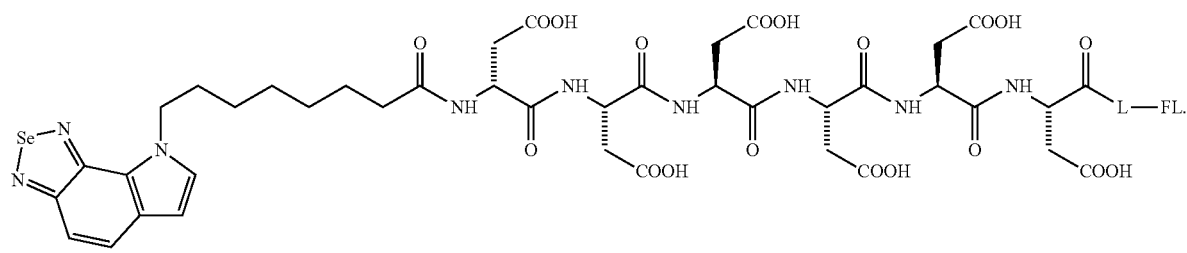
13. The bisubstrate fluorescent probe of claim 1, wherein the structure of the probe is selected from the group consisting of:
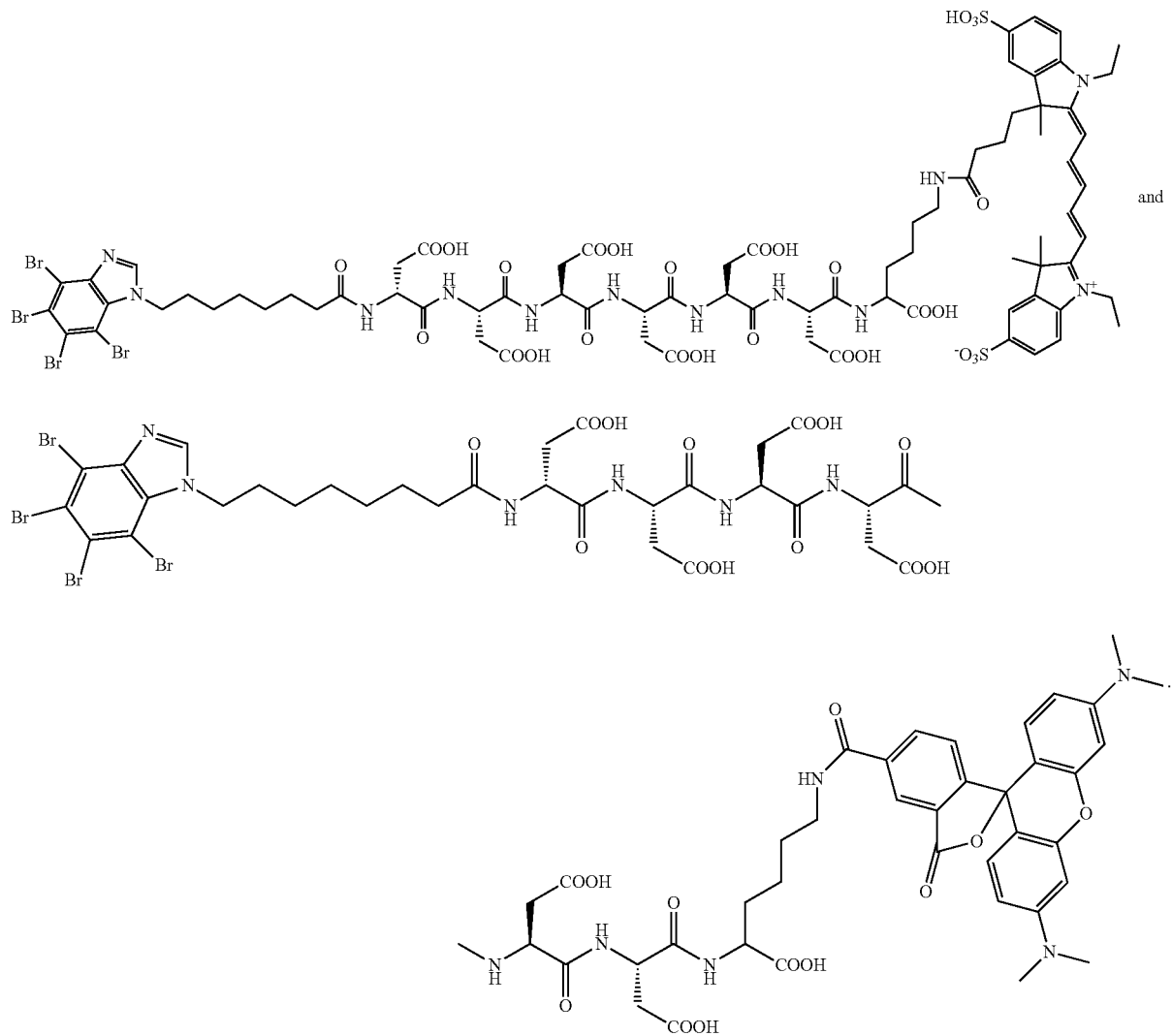

14. The bisubstrate fluorescent probe of claim 1, wherein the structure of the probe is selected from the group consisting of:
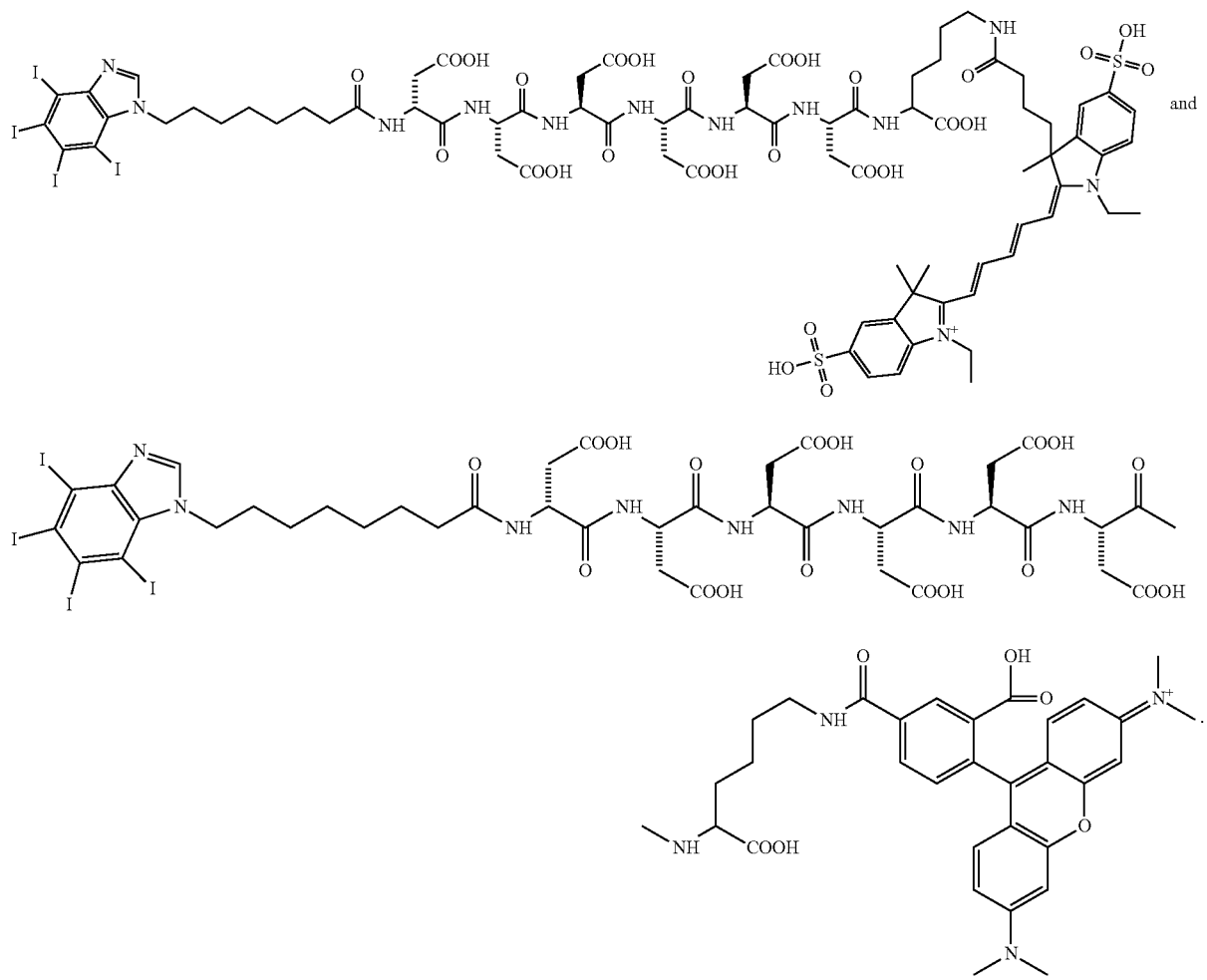
15. The bisubstrate fluorescent probe of claim 1, wherein the structure of the probe is selected from the group consisting of:
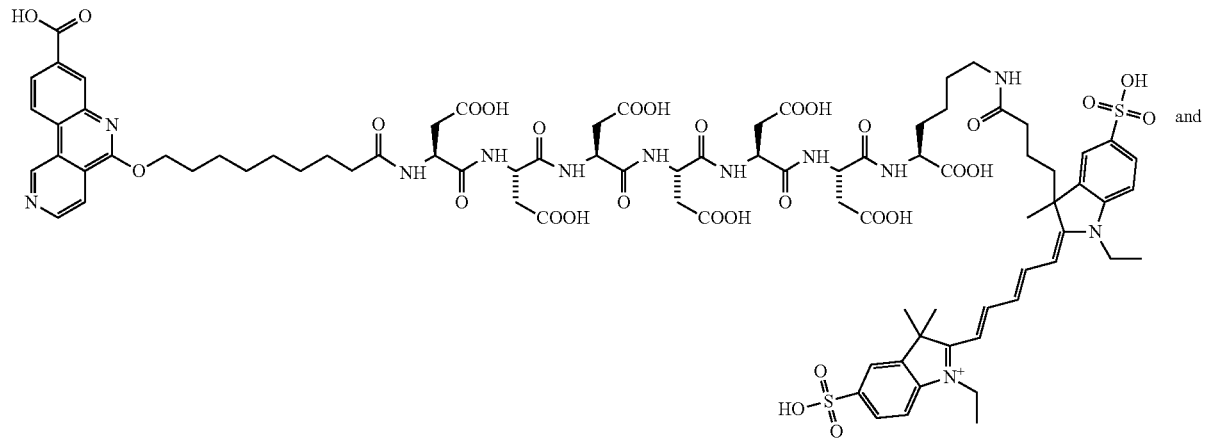

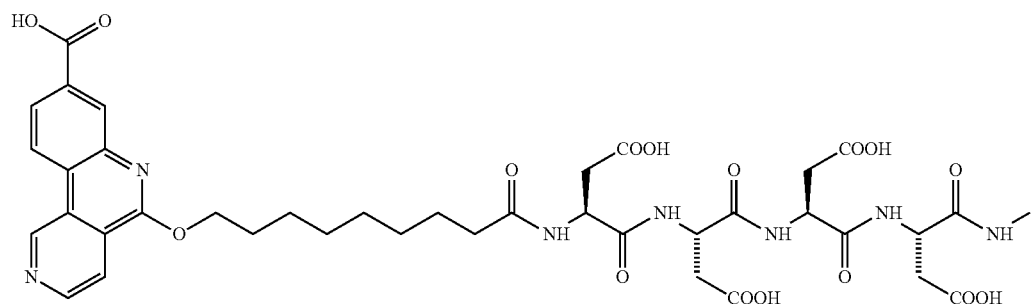
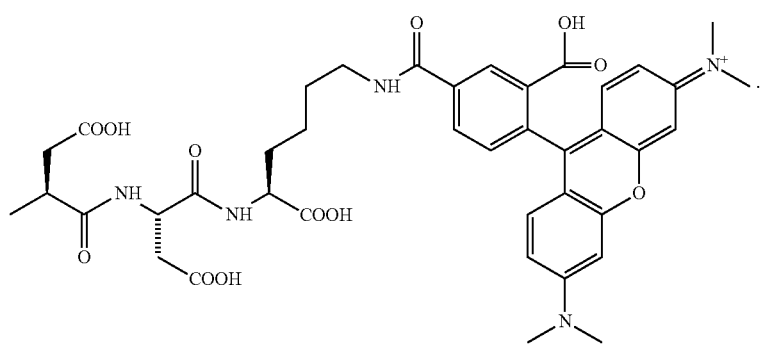
16. The bisubstrate fluorescent probe of claim 1, wherein the structure of the probe is selected from the group consisting of:
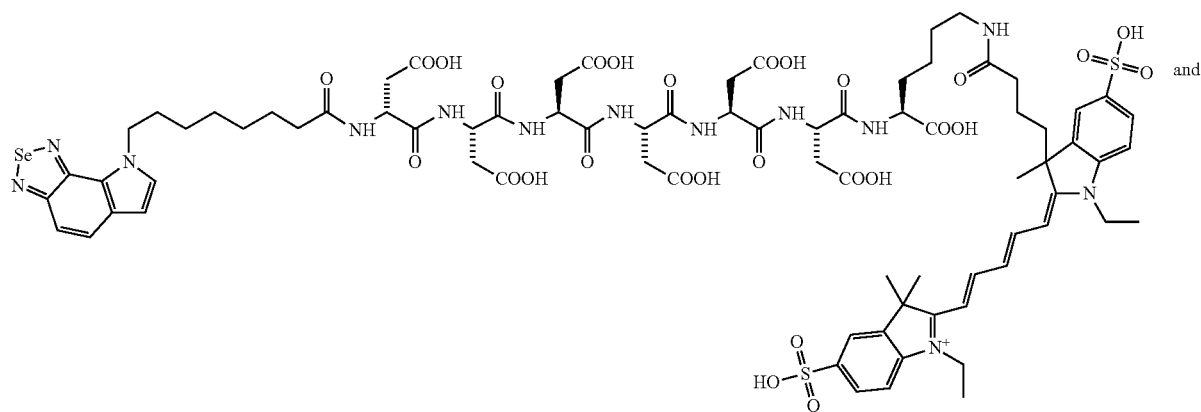
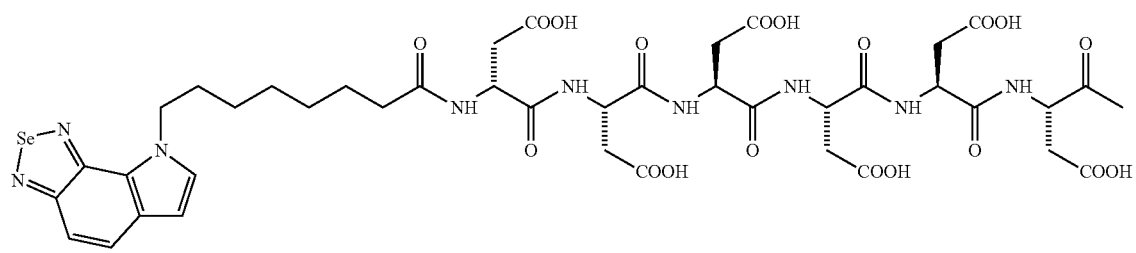

-continued
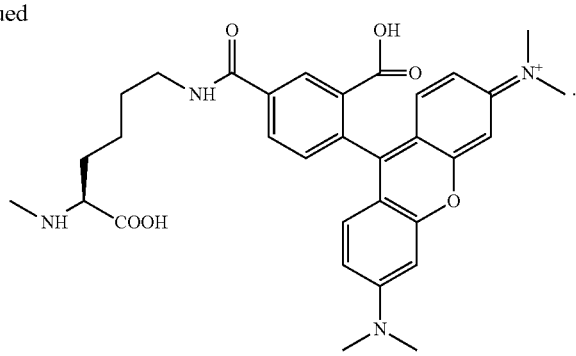

The invention claimed is:

1. A bisubstrate fluorescent probe

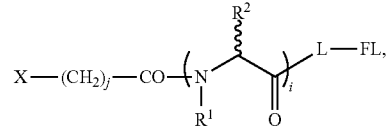

which binds to protein kinase CK2 (casein kinase 2) with affinity KD=0.02-10 nm and wherein fragment X is 1H-benzimidazol or substituted 1H-benzimidazol, j is from 1 to 10, i is from 1 to 10, $R^1$ and $R^2$ are independently H or —(CH$_2$)$_n$COOH, n is independently 0 to 3, at least one of $R^1$ and $R^2$ is —(CH$_2$)$_n$COOH, and the α-carbon connected to $R^2$ is independently in either R or S configuration, FL is a fluorescent label, and L is a linker formed of a hydrocarbon chain.

2. The bisubstrate fluorescent probe of claim 1, wherein X is substituted 1H-benzimidazol with one to four halogeno groups.

3. The bisubstrate fluorescent probe of claim 1, wherein X is tetrabromo-1H-benzimidazol.

4. The bisubstrate fluorescent probe of claim 1 wherein X is tetraiodo-1H-benzimidazol.

5. The bisubstrate fluorescent probe of claim 1, wherein X is 1H-benzimidazole or substituted 1H-benzimidazole connected through the N-atom of the imidazole ring.

6. A bisubstrate fluorescent probe, which binds to protein kinase CK2 (casein kinase 2) with affinity KD=0.02-10 nm and wherein fragment X is

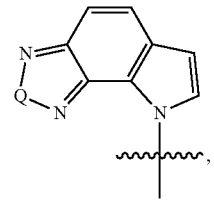

j is from 1 to 10, i is from 1 to 10, $R^1$ and $R^2$ are independently H or —$(CH_2)_n$COOH, n is independently 0 to 3, at least one of $R^1$ and $R^2$ is —$(CH_2)_n$COOH, and the α-carbon connected to $R^2$ is independently in either R or S configuration, FL is a fluorescent label, and L is a linker formed of a hydrocarbon chain.

7. The bisubstrate fluorescent probe of claim 6, wherein Q is S or Se.

8. A bisubstrate fluorescent probe, which binds to protein kinase CK2 (casein kinase 2) with affinity KD=0.02-10 nm and wherein fragment X is

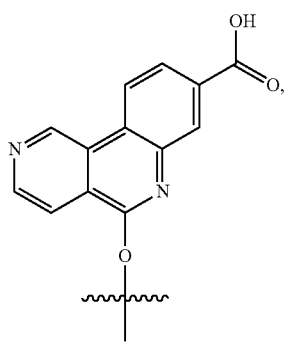 [SMILES: *Oc1nc2cc(C(=O)O)ccc2c2cnccc12]

j is from 1 to 10, i is from 1 to 10, $R^1$ and $R^2$ are independently H or —$(CH_2)_n$COOH, n is independently 0 to 3, at least one of $R^1$ and $R^2$ is —$(CH_2)_n$COOH, and the α-carbon connected to $R^2$ is independently in either R or S configuration, FL is a fluorescent label, and L is a linker formed of a hydrocarbon chain.

9. The bisubstrate fluorescent probe of claim 1, wherein the structure of the probe is

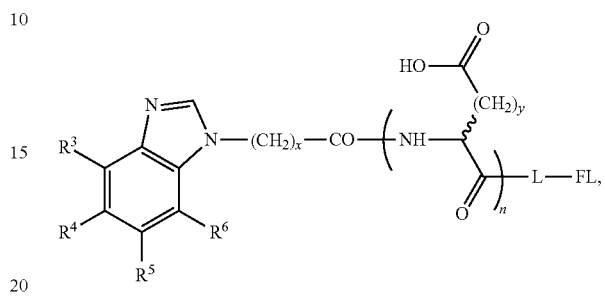

wherein R3, R4, R5 and R6 are selected from H, Br or I, x is from 1 to 10, y is independently from 0 to 3, n is 1 to 10, stereo-centers are independently in either R or S configuration.

10. The bisubstrate fluorescent probe of claim 1, wherein the structure of the probe is selected from the group consisting of:

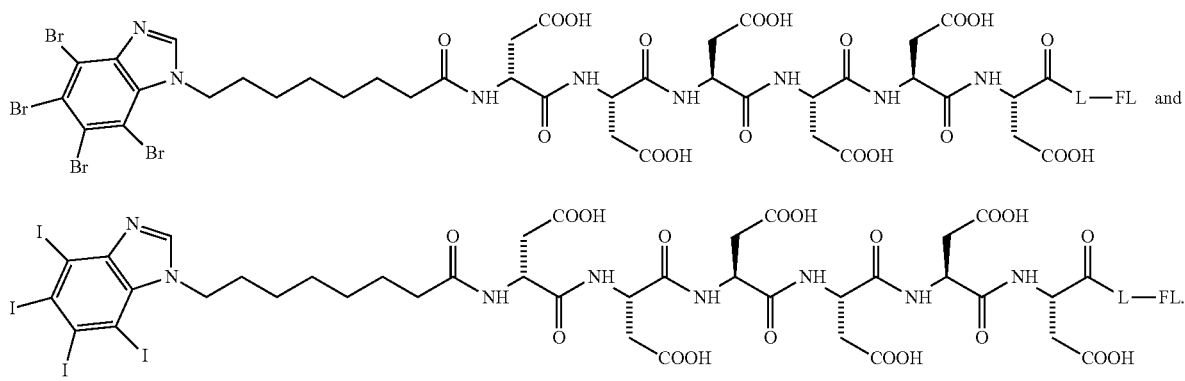

11. The bisubstrate fluorescent probe of claim 1, wherein the structure of the probe is selected from the group consisting of: